US011345900B2

(12) United States Patent
Zhang et al.

(10) Patent No.: US 11,345,900 B2
(45) Date of Patent: May 31, 2022

(54) MONOOXYGENASE AND USE IN PREPARATION OF OPTICALLY PURE SULFOXIDE

(71) Applicants: JIANGSU AOSAIKANG PHARMACEUTICAL CO., LTD., Nanjing (CN); EAST CHINA UNIVERSITY OF SCIENCE AND TECHNOLOGY, Shanghai (CN)

(72) Inventors: Yan Zhang, Nanjing (CN); Huilei Yu, Nanjing (CN); Shimiao Ren, Nanjing (CN); Peng Zhao, Nanjing (CN); Jianhe Xu, Nanjing (CN); Yinqi Wu, Nanjing (CN); Qian Zhao, Nanjing (CN)

(73) Assignees: JIANGSU AOSAIKANG PHARMACEUTICAL CO., LTD., Nanjing (CN); EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 17/294,424

(22) PCT Filed: Nov. 26, 2019

(86) PCT No.: PCT/CN2019/120798

§ 371 (c)(1),
(2) Date: May 17, 2021

(87) PCT Pub. No.: WO2020/108462

PCT Pub. Date: Jun. 4, 2020

(65) Prior Publication Data

US 2022/0002684 A1 Jan. 6, 2022

(30) Foreign Application Priority Data

Nov. 26, 2018 (CN) ........................ 201811420321.1

(51) Int. Cl.
*C12N 9/02* (2006.01)
*C12P 17/14* (2006.01)
*C12P 17/16* (2006.01)

(52) U.S. Cl.
CPC .......... *C12N 9/0071* (2013.01); *C12P 17/165* (2013.01); *C12Y 114/14001* (2013.01)

(58) Field of Classification Search
CPC ........ C12N 9/0073; C12P 11/00; C12P 13/02; C12P 41/002; C12Y 114/13022
USPC ............. 435/117, 122, 129, 130, 189, 252.3, 435/320.1
See application file for complete search history.

(56) References Cited

FOREIGN PATENT DOCUMENTS

| | | | |
|---|---|---|---|
| CN | 101372676 | A | 2/2009 |
| CN | 101372676 | B | 8/2010 |
| CN | 102884178 | A | 1/2013 |
| CN | 108118035 | A | 6/2018 |
| WO | 2011071982 | A2 | 6/2011 |

OTHER PUBLICATIONS

Devos et al., (Proteins: Structure, Function and Genetics, 2000, vol. 41: 98-107.*

Whisstock et al., Quarterly Reviews of Biophysics 2003, vol. 36 (3): 307-340.*

Witkowski et al., Biochemistry 38:11643-11650, 1999.*

Kisselev L., (Structure, 2002, vol. 10: 8-9.*

Peter Babiak, et al., Whole-cell oxidation of omeprazole sulfide to enantiopure esomeprazole with *Lysinibacillus* sp. B71, Bioresource Technology, 2011, pp. 7621-7626, 102.

WP_045432192, NAD(P)/FAD-dependent oxidoreductase [Acinetobacter calcoaceticus], 2018.

* cited by examiner

*Primary Examiner* — Robert B Mondesi
*Assistant Examiner* — Mohammad Y Meah
(74) *Attorney, Agent, or Firm* — Bayramoglu Law Offices LLC

(57) ABSTRACT

A monooxygenase having an amino acid sequence obtained by mutation of the amino acid sequence shown in SEQ ID NO:2 is disclosed. The use of the monooxygenase of the present invention in production of chiral sulfoxide-based drugs has advantages including mild reaction conditions, environmental friendliness, high yield, high optical purity of products, less peroxide products, and the like, and therefore the monooxygenase in the present invention has a good industrial application prospect in the production of proton pump inhibitors for the treatment of gastric ulcers.

14 Claims, 3 Drawing Sheets

Specification includes a Sequence Listing.

SEQUENCE LISTING

<160> NUMBER OF SEQ ID NOS: 98

<210> SEQ ID NO 1
<211> LENGTH: 1629
<212> TYPE: DNA
<213> ORGANISM: Acinetobacter calcoaceticus

<400> SEQUENCE: 1
atgacccaga agatggactt tgatgcgatc attatcggcg cgggtttcgg tggcctgtac 60
agcctgaaga aactgcgtga cgattttaac ctgaaagtgc gtgcgttcga tcgtgcgacc 120
gaggttggtg gcacctggtt ttggaaccaa tatccgggtg cgctgagcga cagcgagacc 180
cacctgtact gctatagctg ggataaggaa ctgctgcagg agatggaaat taagcgtaag 240
tacatcagcc aaccggacgt gctggcgtat ctgaaacgtg ttgcggacaa gcacgatctg 300
cgtaaagaca ttcagttcga aaccggcatc cgtagcgcgt actttgatga ggaaaacagc 360
ttctggaacg tgaccaccga gaacgacgaa aagtttaccg cgcgtttcct gatcaccgcg 420
ctgggtctgc tggcggcgcc gaacctgccg aaaattaagg gcatcgagac ctttaaaggt 480
gaactgcacc acaccagccg ttggccgaag gacgttacct tcagcggcaa acgtgtgggt 540
gttattggca ccggtagcac cggcgtgcag gttattaccg cgatcgcgag ccaagtgaaa 600
cacctgaccg tttttcagcg tagcgcgcaa tacagcgtgc cgatcggtaa cgtggttatg 660
agcgagaccg acgttgcgaa aattaaggag aactatgatc aaatctggga aaacgtgtgg 720
aacagcgcgc tgggcttcgg tctgaacgaa agcaccctgc cgaccatgag cgttagcgcg 780
gaggaacgtg ataaaatttt tgagaaggcg tggcaggaag gtggcggttt ccgttttatg 840
ttcgagacct tcggtgacat cgcggtggat gagaccgcga acattgaagc gcaaaacttc 900
atcaagaaaa agattagcga aatcgtgaag gacccgttcg ttgcgaaaaa gctgaccccg 960
accgacctgt acgcgaaacg tccgctgtgc gatagcggct actatgagat ttttaaccgt 1020
gacaacgtga gcctggaaga tgttaaggcg aacccgattg tggagatcaa agaagactgc 1080
gtggttaccg cggatggtgt tgagcacaag ctggatatgc tgatctgcgc gaccggcttc 1140
gacgcggttg atggtaacta cattcgtatg gacatccgtg gcaaagatgg tattagcatc 1200
aaagaccact ggaaggatgg cccgaacagc tatctgggta tgatggttag caactttccg 1260
aacatgttca tggttctggg cccgaacggt ccgttcacca acctgccgcc gagcatcgag 1320
acccaagtgc gttggattgc ggacctgatc ggctatgcgg aggatcacca gattaaccaa 1380
atcgaagcga ccaaggacgc ggttgataac tggaccaaca cctgcagcga cattgcgaac 1440
aagaccctgt ttgcgaaagc ggaaagctgg atcttcggcg cgaacgtgcc gggtaaaaag 1500
aacaccgttt acttctatat gggcggtctg aaagagtacc gtaaccagat tagcgaagtg 1560
agcaacaaca actataaggg ttgcctgctg aaacaaagcg ttaaaaagac caacctgatc 1620
gaaagctaa 1629

<210> SEQ ID NO 2
<211> LENGTH: 542
<212> TYPE: PRT
<213> ORGANISM: Acinetobacter calcoaceticus

<400> SEQUENCE: 2

Met Thr Gln Lys Met Asp Phe Asp Ala Ile Ile Ile Gly Ala Gly Phe
1 5 10 15

Gly Gly Leu Tyr Ser Leu Lys Lys Leu Arg Asp Asp Phe Asn Leu Lys
20 25 30

```
Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Lys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Leu Gly Pro Asn Gly Pro Phe
            420                 425                 430

Thr Asn Leu Pro Pro Ser Ile Glu Thr Gln Val Arg Trp Ile Ala Asp
        435                 440                 445
```

```
Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 3
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 3

atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggttctggg cccgaacggt ccgctgacca acctgccgcc gagcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acttctatat gggcggtctg aaagagtacc gtaaccagat tagcgaagtg   1560
```

```
agcaacaaca actataaggg ttgcctgctg aaacaaagcg ttaaaaagac caacctgatc   1620

gaaagctaa                                                           1629


<210> SEQ ID NO 4
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 4

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
```

```
        340                 345                 350

Ile Val Glu Ile Lys Glu Asp Cys Val Val Thr Ala Asp Gly Val Glu
    355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Leu Gly Pro Asn Gly Pro Leu
            420                 425                 430

Thr Asn Leu Pro Pro Ser Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 5
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 5

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960
```

```
accgacctgt acgcgttccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggttctggg cccgaacggt ccgctgacca acctgccgcc gagcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acttctatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

```
<210> SEQ ID NO 6
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 6

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240
```

```
Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Phe Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Leu Gly Pro Asn Gly Pro Leu
            420                 425                 430

Thr Asn Leu Pro Pro Ser Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 7
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 7

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360
```

```
ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat tttaaccgt    1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggttctggg cccgaacggt ccgatcacca acctgccgcc gagcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acttctatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                            1629
```

```
<210> SEQ ID NO 8
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 8

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125
```

```
Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Leu Gly Pro Asn Gly Pro Ile
            420                 425                 430

Thr Asn Leu Pro Pro Ser Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 9
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 9

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggttctggg cccgaacggt ccgctgacca acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acttctatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 10
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 10

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
```

```
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Leu Gly Pro Asn Gly Pro Leu
            420                 425                 430

Thr Asn Ser Pro Pro Ile Ile Glu Thr Gln Val Arg Trp Ile Ala Asp
        435                 440                 445
```

```
Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 11
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 11

atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtctgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggcttcgg tctgaacgaa agcaccctgc cgaccatgag cgttagcgcg     780

gaggaacgtg ataaaatttt tgagaaggcg tggcaggaag gtggcggttt ccgttttatg     840

ttcgagacct tcggtgacat cgcggtggat gagaccgcga acattgaagc gcaaaacttc     900

atcaagaaaa agattagcga aatcgtgaag gacccgttcg ttgcgaaaaa gctgaccccg     960

accgacctgt acgcgttccg tccgctgtgc gatagcggct actatgagat ttttaaccgt    1020

gacaacgtga gcctggaaga tgttaaggcg aaccccgattg tggagatcaa agaagactgc    1080

gtggttaccg cggatggtgt tgagcacaag ctggatatgc tgatctgcgc gaccggcttc    1140

gacgcggttg atggtaacta cattcgtatg gacatccgtg gcaaagatgg tattagcatc    1200

aaagaccact ggaaggatgg cccgaacagc tatctgggta tgatggttag caactttccg    1260

aacatgttca tggttctggg cccgaacggt ccgctgacca acagcccgcc gatcatcgag    1320

acccaagtgc gttggattgc ggacctgatc ggctatgcgg aggatcacca gattaaccaa    1380

atcgaagcga ccaaggacgc ggttgataac tggaccaaca cctgcagcga cattgcgaac    1440

aagaccctgt ttgcgaaagc ggaaagctgg atcttcggcg cgaacgtgcc gggtaaaaag    1500
```

```
aacaccgttt acttctatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629


<210> SEQ ID NO 12
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 12

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Phe Arg Pro Leu Cys Asp Ser Gly Tyr Tyr Glu
                325                 330                 335
```

```
Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Leu Gly Pro Asn Gly Pro Leu
            420                 425                 430

Thr Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 13
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 13

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900
```

```
atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggttctggg cccgaacggt ccgctgtgca acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acttctatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                            1629
```

<210> SEQ ID NO 14
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 14

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
```

```
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Leu Gly Pro Asn Gly Pro Leu
            420                 425                 430

Cys Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 15
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 15

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300
```

```
cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggttctggg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acttctatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 16
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 16

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125
```

```
Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Leu Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

```
<210> SEQ ID NO 17
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 17

atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acttctatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629


<210> SEQ ID NO 18
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 18

Met Thr Gln Lys Met Asp Phe Asp Ala Ile Ile Ile Gly Ala Gly Phe
1               5                   10                  15
```

-continued

```
Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
```

```
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 19
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 19

atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggttccggg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500
```

```
aacaccgttt acttctatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                            1629


<210> SEQ ID NO 20
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 20

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335
```

```
Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Pro Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Phe Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 21
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 21

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtctgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggcttcgg tctgaacgaa agcaccctgc cgaccatgag cgttagcgcg     780

gaggaacgtg ataaaatttt tgagaaggcg tggcaggaag gtggcggttt ccgttttatg     840

ttcgagacct tcggtgacat cgcggtggat gagaccgcga acattgaagc gcaaaacttc     900
```

```
atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

```
<210> SEQ ID NO 22
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 22

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220
```

```
Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 23
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 23

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300
```

```
cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 24
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 24

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
```

```
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 25
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 25

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtgcgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 26
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 26

```
Met Thr Gln Lys Met Asp Phe Asp Ala Ile Ile Ile Gly Ala Gly Phe
1               5                   10                  15
```

```
Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Ala Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430
```

```
Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 27
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 27

atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtctgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgg ttggcttcgg tctgaacgaa agcaccctgc cgaccatgag cgttagcgcg     780

gaggaacgtg ataaaatttt tgagaaggcg tggcaggaag gtggcggttt ccgttttatg     840

ttcgagacct tcggtgacat cgcggtggat gagaccgcga acattgaagc gcaaaacttc     900

atcaagaaaa agattagcga aatcgtgaag gacccgttcg ttgcgaaaaa gctgaccccg     960

accgacctgt acgcgtgccg tccgctgtgc gatagcggct actatgagat ttttaaccgt    1020

gacaacgtga gcctggaaga tgttaaggcg aacccgattg tggagatcaa agaagactgc    1080

gtggttaccg cggatggtgt tgagcacaag ctggatatgc tgatctgcgc gaccggcttc    1140

gacgcggttg atggtaacta cattcgtatg gacatccgtg gcaaagatgg tattagcatc    1200

aaagaccact ggaaggatgg cccgaacagc tatctgggta tgatggttag caactttccg    1260

aacatgttca tggtttttgg cccgaacggt ccgctggcga acagcccgcc gatcatcgag    1320

acccaagtgc gttggattgc ggacctgatc ggctatgcgg aggatcacca gattaaccaa    1380

atcgaagcga ccaaggacgc ggttgataac tggaccaaca cctgcagcga cattgcgaac    1440
```

aagaccctgt ttgcgaaagc ggaaagctgg atcttcggcg cgaacgtgcc gggtaaaaag 1500
aacaccgttt acctgtatat gggcggtctg aaagagtacc gtaaccagat tagcgaagtg 1560
agcaacaaca actataaggg ttgcctgctg aaacaaagcg ttaaaaagac caacctgatc 1620
gaaagctaa 1629

<210> SEQ ID NO 28
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 28

Met Thr Gln Lys Met Asp Phe Asp Ala Ile Ile Ile Gly Ala Gly Phe
1 5 10 15

Gly Gly Leu Tyr Ser Leu Lys Lys Leu Arg Asp Asp Phe Asn Leu Lys
20 25 30

Val Arg Ala Phe Asp Arg Ala Thr Glu Val Gly Gly Thr Trp Phe Trp
35 40 45

Asn Gln Tyr Pro Gly Ala Leu Ser Asp Ser Glu Thr His Leu Tyr Cys
50 55 60

Tyr Ser Trp Asp Lys Glu Leu Leu Gln Glu Met Glu Ile Lys Arg Lys
65 70 75 80

Tyr Ile Ser Gln Pro Asp Val Leu Ala Tyr Leu Lys Arg Val Ala Asp
85 90 95

Lys His Asp Leu Arg Lys Asp Ile Gln Phe Glu Thr Gly Ile Arg Ser
100 105 110

Ala Tyr Phe Asp Glu Glu Asn Ser Phe Trp Asn Val Thr Thr Glu Asn
115 120 125

Asp Glu Lys Phe Thr Ala Arg Phe Leu Ile Thr Ala Leu Gly Leu Leu
130 135 140

Ala Ala Pro Asn Leu Pro Lys Ile Lys Gly Ile Glu Thr Phe Lys Gly
145 150 155 160

Glu Leu His His Thr Ser Arg Trp Pro Lys Asp Val Thr Phe Ser Gly
165 170 175

Lys Arg Val Gly Val Ile Gly Thr Gly Ser Thr Gly Val Gln Val Ile
180 185 190

Thr Ala Ile Ala Ser Gln Val Lys His Leu Thr Val Phe Gln Arg Ser
195 200 205

Ala Gln Tyr Ser Val Pro Ile Gly Asn Val Val Met Ser Glu Thr Asp
210 215 220

Val Ala Lys Ile Lys Glu Asn Tyr Asp Gln Ile Trp Glu Asn Val Trp
225 230 235 240

Asn Ser Ala Val Gly Phe Gly Leu Asn Glu Ser Thr Leu Pro Thr Met
245 250 255

Ser Val Ser Ala Glu Glu Arg Asp Lys Ile Phe Glu Lys Ala Trp Gln
260 265 270

Glu Gly Gly Gly Phe Arg Phe Met Phe Glu Thr Phe Gly Asp Ile Ala
275 280 285

Val Asp Glu Thr Ala Asn Ile Glu Ala Gln Asn Phe Ile Lys Lys Lys
290 295 300

Ile Ser Glu Ile Val Lys Asp Pro Phe Val Ala Lys Lys Leu Thr Pro
305 310 315 320

Thr Asp Leu Tyr Ala Cys Arg Pro Leu Cys Asp Ser Gly Tyr Tyr Glu

```
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 29
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 29

atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtctgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcga tcggcttcgg tctgaacgaa agcaccctgc cgaccatgag cgttagcgcg     780

gaggaacgtg ataaaatttt tgagaaggcg tggcaggaag gtggcggttt ccgttttatg     840
```

```
ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 30
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 30

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220
```

```
Val Ala Lys Ile Lys Glu Asn Tyr Asp Gln Ile Trp Glu Asn Val Trp
225                 230                 235                 240

Asn Ser Ala Ile Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 31
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 31

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240
```

```
tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tgaaaacgaa agcaccctgc cgaccatgag cgttagcgcg    780

gaggaacgtg ataaaatttt tgagaaggcg tggcaggaag gtggcggttt ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 32
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 32

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110
```

```
Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Glu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
```

530 535 540

<210> SEQ ID NO 33
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 33
atgacccaga agatggactt tgatgcgatc attatcggcg cgggtttcgg tggcctgtac 60
agcctgaaga aactgcgtga cgattttaac ctgaaagtgc gtgcgttcga tcgtgcgacc 120
gaggttggtg gcacctggtt ttggaaccaa tatccgggtg cgctgagcga cagcgagacc 180
cacctgtact gctatagctg ggataaggaa ctgctgcagg agatggaaat taagcgtaag 240
tacatcagcc aaccggacgt gctggcgtat ctgaaacgtg ttgcggacaa gcacgatctg 300
cgtaaagaca ttcagttcga aaccggcatc cgtagcgcgt actttgatga ggaaaacagc 360
ttctggaacg tgaccaccga gaacgacgaa aagtttaccg cgcgtttcct gatcaccgcg 420
ctgggtctgc tggcggcgcc gaacctgccg aaaattaagg gcatcgagac ctttaaaggt 480
gaactgcacc acaccagccg ttggccgaag gacgttacct tcagcggcaa acgtgtgggt 540
gttattggca ccggtagcac cggcgtgcag gttattaccg cgatcgcgag ccaagtgaaa 600
cacctgaccg tttttcagcg tagcgcgcaa tacagcgtgc cgatcggtaa cgtggttatg 660
agcgagaccg acgttgcgaa aattaaggag aactatgatc aaatctggga aaacgtgtgg 720
aacagcgcgc tgggcttcgg taacaacgaa agcaccctgc cgaccatgag cgttagcgcg 780
gaggaacgtg ataaaatttt tgagaaggcg tggcaggaag gtggcggttt ccgttttatg 840
ttcgagacct tcggtgacat cgcggtggat gagaccgcga acattgaagc gcaaaacttc 900
atcaagaaaa agattagcga aatcgtgaag gacccgttcg ttgcgaaaaa gctgaccccg 960
accgacctgt acgcgtgccg tccgctgtgc gatagcggct actatgagat ttttaaccgt 1020
gacaacgtga gcctggaaga tgttaaggcg aacccgattg tggagatcaa agaagactgc 1080
gtggttaccg cggatggtgt tgagcacaag ctggatatgc tgatctgcgc gaccggcttc 1140
gacgcggttg atggtaacta cattcgtatg gacatccgtg gcaaagatgg tattagcatc 1200
aaagaccact ggaaggatgg cccgaacagc tatctgggta tgatggttag caactttccg 1260
aacatgttca tggtttttgg cccgaacggt ccgctggcga acagcccgcc gatcatcgag 1320
acccaagtgc gttggattgc ggacctgatc ggctatgcgg aggatcacca gattaaccaa 1380
atcgaagcga ccaaggacgc ggttgataac tggaccaaca cctgcagcga cattgcgaac 1440
aagaccctgt ttgcgaaagc ggaaagctgg atcttcggcg cgaacgtgcc gggtaaaaag 1500
aacaccgttt acctgtatat gggcggtctg aaagagtacc gtaaccagat tagcgaagtg 1560
agcaacaaca actataaggg ttgcctgctg aaacaaagcg ttaaaaagac caacctgatc 1620
gaaagctaa 1629

<210> SEQ ID NO 34
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 34

Met Thr Gln Lys Met Asp Phe Asp Ala Ile Ile Ile Gly Ala Gly Phe

-continued

```
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Asn Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430
```

```
Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 35
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 35

atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtctgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggcttcgg tgcgaacgaa agcaccctgc cgaccatgag cgttagcgcg     780

gaggaacgtg ataaaatttt tgagaaggcg tggcaggaag gtggcggttt ccgttttatg     840

ttcgagacct tcggtgacat cgcggtggat gagaccgcga acattgaagc gcaaaacttc     900

atcaagaaaa agattagcga aatcgtgaag gacccgttcg ttgcgaaaaa gctgaccccg     960

accgacctgt acgcgtgccg tccgctgtgc gatagcggct actatgagat ttttaaccgt    1020

gacaacgtga gcctggaaga tgttaaggcg aacccgattg tggagatcaa agaagactgc    1080

gtggttaccg cggatggtgt tgagcacaag ctggatatgc tgatctgcgc gaccggcttc    1140

gacgcggttg atggtaacta cattcgtatg gacatccgtg gcaaagatgg tattagcatc    1200

aaagaccact ggaaggatgg cccgaacagc tatctgggta tgatggttag caactttccg    1260

aacatgttca tggtttttgg cccgaacggt ccgctggcga acagcccgcc gatcatcgag    1320

acccaagtgc gttggattgc ggacctgatc ggctatgcgg aggatcacca gattaaccaa    1380

atcgaagcga ccaaggacgc ggttgataac tggaccaaca cctgcagcga cattgcgaac    1440
```

```
aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629


<210> SEQ ID NO 36
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 36

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Ala Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320
```

```
Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 37
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 37

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtctgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggcttcgg ttggaacgaa agcaccctgc cgaccatgag cgttagcgcg     780

gaggaacgtg ataaaatttt tgagaaggcg tggcaggaag gtggcggttt ccgttttatg     840
```

```
ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

```
<210> SEQ ID NO 38
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 38

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
```

```
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Trp Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 39
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 39

atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240
```

```
tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 40
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 40

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110
```

```
Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525
```

```
Leu Leu Lys Gln Ser Val Lys Lys Thr Asn Leu Ile Glu Ser
    530                 535                 540
```

<210> SEQ ID NO 41
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 41

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggtgt gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 42
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 42

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Val Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
```

```
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 43
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 43

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggtta ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380
```

atcgaagcga ccaaggacgc ggttgataac tggaccaaca cctgcagcga cattgcgaac 1440
aagaccctgt ttgcgaaagc ggaaagctgg atcttcggcg cgaacgtgcc gggtaaaaag 1500
aacaccgttt acctgtatat gggcggtctg aaagagtacc gtaaccagat tagcgaagtg 1560
agcaacaaca actataaggg ttgcctgctg aaacaaagcg ttaaaaagac caacctgatc 1620
gaaagctaa 1629

<210> SEQ ID NO 44
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 44

Met Thr Gln Lys Met Asp Phe Asp Ala Ile Ile Ile Gly Ala Gly Phe
1 5 10 15

Gly Gly Leu Tyr Ser Leu Lys Lys Leu Arg Asp Asp Phe Asn Leu Lys
20 25 30

Val Arg Ala Phe Asp Arg Ala Thr Glu Val Gly Gly Thr Trp Phe Trp
35 40 45

Asn Gln Tyr Pro Gly Ala Leu Ser Asp Ser Glu Thr His Leu Tyr Cys
50 55 60

Tyr Ser Trp Asp Lys Glu Leu Leu Gln Glu Met Glu Ile Lys Arg Lys
65 70 75 80

Tyr Ile Ser Gln Pro Asp Val Leu Ala Tyr Leu Lys Arg Val Ala Asp
85 90 95

Lys His Asp Leu Arg Lys Asp Ile Gln Phe Glu Thr Gly Ile Arg Ser
100 105 110

Ala Tyr Phe Asp Glu Glu Asn Ser Phe Trp Asn Val Thr Thr Glu Asn
115 120 125

Asp Glu Lys Phe Thr Ala Arg Phe Leu Ile Thr Ala Leu Gly Pro Leu
130 135 140

Ala Ala Pro Asn Leu Pro Lys Ile Lys Gly Ile Glu Thr Phe Lys Gly
145 150 155 160

Glu Leu His His Thr Ser Arg Trp Pro Lys Asp Val Thr Phe Ser Gly
165 170 175

Lys Arg Val Gly Val Ile Gly Thr Gly Ser Thr Gly Val Gln Val Ile
180 185 190

Thr Ala Ile Ala Ser Gln Val Lys His Leu Thr Val Phe Gln Arg Ser
195 200 205

Ala Gln Tyr Ser Val Pro Ile Gly Asn Val Val Met Ser Glu Thr Asp
210 215 220

Val Ala Lys Ile Lys Glu Asn Tyr Asp Gln Ile Trp Glu Asn Val Trp
225 230 235 240

Asn Ser Ala Leu Gly Phe Gly Leu Asn Glu Ser Thr Leu Pro Thr Met
245 250 255

Ser Val Ser Ala Glu Glu Arg Asp Lys Ile Phe Glu Lys Ala Trp Gln
260 265 270

Glu Gly Gly Gly Tyr Arg Phe Met Phe Glu Thr Phe Gly Asp Ile Ala
275 280 285

Val Asp Glu Thr Ala Asn Ile Glu Ala Gln Asn Phe Ile Lys Lys Lys
290 295 300

Ile Ser Glu Ile Val Lys Asp Pro Phe Val Ala Lys Lys Leu Thr Pro
305 310 315 320

```
Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 45
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 45

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtctgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggcttcgg tctgaacgaa agcaccctgc cgaccatgag cgttagcgcg     780
```

```
gaggaacgtg ataaaatttt tgagaaggcg tggcaggaag gtggcggtat ccgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 46
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 46

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205
```

```
Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Ile Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 47
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 47

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180
```

```
cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggtga tcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

```
<210> SEQ ID NO 48
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 48

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
```

```
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Asp Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525
```

```
Leu Leu Lys Gln Ser Val Lys Lys Thr Asn Leu Ile Glu Ser
    530                 535                 540


<210> SEQ ID NO 49
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 49

atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

gtggagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629


<210> SEQ ID NO 50
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 50
```

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Val Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415
```

```
Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 51
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 51

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtctgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggttt ccgttttatg    840

gcggagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380
```

```
atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 52
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 52

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Leu Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Phe Arg Phe Met Ala Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
```

```
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 53
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 53

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtccgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggcttcgg tctgaacgaa agcaccctgc cgaccatgag cgttagcgcg     780
```

```
gaggaacgtg ataaaatttt tgagaaggcg tggcaggaag gtggcggtct gcgttttatg    840

gttgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 54
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 54

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205
```

```
Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Val Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 55
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 55

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180
```

```
cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggtgt tcgttttatg    840

gcggagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 56
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 56

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95
```

```
Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Val Arg Phe Met Ala Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
```

515 520 525

Leu Leu Lys Gln Ser Val Lys Lys Thr Asn Leu Ile Glu Ser
530 535 540

<210> SEQ ID NO 57
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 57
atgacccaga agatggactt tgatgcgatc attatcggcg cgggtttcgg tggcctgtac 60
agcctgaaga aactgcgtga cgattttaac ctgaaagtgc gtgcgttcga tcgtgcgacc 120
gaggttggtg gcacctggtt ttggaaccaa tatccgggtg cgctgagcga cagcgagacc 180
cacctgtact gctatagctg ggataaggaa ctgctgcagg agatggaaat taagcgtaag 240
tacatcagcc aaccggacgt gctggcgtat ctgaaacgtg ttgcggacaa gcacgatctg 300
cgtaaagaca ttcagttcga aaccggcatc cgtagcgcgt actttgatga ggaaaacagc 360
ttctggaacg tgaccaccga gaacgacgaa aagtttaccg cgcgtttcct gatcaccgcg 420
ctgggtccgc tggcggcgcc gaacctgccg aaaattaagg gcatcgagac ctttaaaggt 480
gaactgcacc acaccagccg ttggccgaag gacgttacct tcagcggcaa acgtgtgggt 540
gttattggca ccggtagcac cggcgtgcag gttattaccg cgatcgcgag ccaagtgaaa 600
cacctgaccg tttttcagcg tagcgcgcaa tacagcgtgc cgatcggtaa cgtggttcgt 660
agcgagaccg acgttgcgaa aattaaggag aactatgatc aaatctggga aaacgtgtgg 720
aacagcgcgc tgggcttcgg tctgaacgaa agcaccctgc cgaccatgag cgttagcgcg 780
gaggaacgtg ataaaatttt tgagaaggcg tggcaggaag gtggcggtct gcgttttatg 840
ttcgagacct tcggtgacat cgcggtggat gagaccgcga acattgaagc gcaaaacttc 900
atcaagaaaa agattagcga aatcgtgaag gacccgttcg ttgcgaaaaa gctgaccccg 960
accgacctgt acgcgtgccg tccgctgtgc gatagcggct actatgagat ttttaaccgt 1020
gacaacgtga gcctggaaga tgttaaggcg aacccgattg tggagatcaa agaagactgc 1080
gtggttaccg cggatggtgt tgagcacaag ctggatatgc tgatctgcgc gaccggcttc 1140
gacgcggttg atggtaacta cattcgtatg gacatccgtg gcaaagatgg tattagcatc 1200
aaagaccact ggaaggatgg cccgaacagc tatctgggta tgatggttag caactttccg 1260
aacatgttca tggtttttgg cccgaacggt ccgctggcga acagcccgcc gatcatcgag 1320
acccaagtgc gttggattgc ggacctgatc ggctatgcgg aggatcacca gattaaccaa 1380
atcgaagcga cccgtgacgc ggttgataac tggaccaaca cctgcagcga cattgcgaac 1440
aagaccctgt ttgcgaaagc ggaaagctgg atcttcggcg cgaacgtgcc gggtaaaaag 1500
aacaccgttt acctgtatat gggcggtctg aaagagtacc gtaaccagat tagcgaagtg 1560
agcaacaaca actataaggg ttgcctgctg aaacaaagcg ttaaaaagac caacctgatc 1620
gaaagctaa 1629

<210> SEQ ID NO 58
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 58

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Arg Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415
```

```
Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Arg Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 59
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 59

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtccgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccgcgagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggcttcgg tctgaacgaa agcaccctgc cgaccatgag cgttagcgcg     780

gaggaacgtg ataaaatttt tgagaaggcg tggcaggaag gtggcggtct gcgttttatg     840

ttcgagacct tcggtgacat cgcggtggat gagaccgcga acattgaagc gcaaaacttc     900

atcaagaaaa agattagcga aatcgtgaag gacccgttcg ttgcgaaaaa gctgaccccg     960

accgacctgt acgcgtgccg tccgctgtgc gatagcggct actatgagat ttttaaccgt    1020

gacaacgtga gcctggaaga tgttaaggcg aaccccgattg tggagatcaa agaagactgc    1080

gtggttaccg cggatggtgt tgagcacaag ctggatatgc tgatctgcgc gaccggcttc    1140

gacgcggttg atggtaacta cattcgtatg gacatccgtg gcaaagatgg tattagcatc    1200

aaagaccact ggaaggatgg cccgaacagc tatctgggta tgatggttag caactttccg    1260

aacatgttca tggtttttgg cccgaacggt ccgctggcga acagcccgcc gatcatcgag    1320
```

```
acccaagtgc gttggattgc ggacctgatc ggctatgcgg aggatcacca gattaaccaa   1380

atcgaagcga ccaaagacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 60
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 60

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Ala Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300
```

```
Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 61
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 61

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtccgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720
```

```
aacagcgcgc tgggctacgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 62
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 62

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
```

```
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 63
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 63

atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120
```

```
gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggctttgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggatggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

tacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

```
<210> SEQ ID NO 64
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 64

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95
```

-continued

```
Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Met Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Tyr Thr Val Tyr Leu Tyr Met Gly Gly Leu Lys Glu
            500                 505                 510
```

```
Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 65
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 65

atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcggcac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggctttgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaaagctgg atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629


<210> SEQ ID NO 66
<211> LENGTH: 542
<212> TYPE: PRT
<213> ORGANISM: Artificial Sequence
<220> FEATURE:
<223> OTHER INFORMATION: The sequence is synthesized.
```

<400> SEQUENCE: 66

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Gly Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
```

```
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 67
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 67

atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggctttgg tctgagcgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320
```

acccaagtgc gttggattgc ggacctgatc ggctatgcgg aggatcacca gattaaccaa 1380
atcgaagcga ccaaggacgc ggttgataac tggaccaaca cctgcagcga cattgcgaac 1440
aagaccctgt ttgcgaaagc ggaaagctgg atcttcggcg cgaacgtgcc gggtaaaaag 1500
aacaccgttt acctgtatat gggcggtctg aaagagtacc gtaaccagat tagcgaagtg 1560
agcaacaaca actataaggg ttgcctgctg aaacaaagcg ttaaaaagac caacctgatc 1620
gaaagctaa 1629

<210> SEQ ID NO 68
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 68

Met Thr Gln Lys Met Asp Phe Asp Ala Ile Ile Ile Gly Ala Gly Phe
1 5 10 15

Gly Gly Leu Tyr Ser Leu Lys Lys Leu Arg Asp Asp Phe Asn Leu Lys
20 25 30

Val Arg Ala Phe Asp Arg Ala Thr Glu Val Gly Gly Thr Trp Phe Trp
35 40 45

Asn Gln Tyr Pro Gly Ala Leu Ser Asp Ser Glu Thr His Leu Tyr Cys
50 55 60

Tyr Ser Trp Asp Lys Glu Leu Leu Gln Glu Met Glu Ile Lys Arg Lys
65 70 75 80

Tyr Ile Ser Gln Pro Asp Val Leu Ala Tyr Leu Lys Arg Val Ala Asp
85 90 95

Lys His Asp Leu Arg Lys Asp Ile Gln Phe Glu Thr Gly Ile Arg Ser
100 105 110

Ala Tyr Phe Asp Glu Glu Asn Ser Phe Trp Asn Val Thr Thr Glu Asn
115 120 125

Asp Glu Lys Phe Thr Ala Arg Phe Leu Ile Thr Ala Leu Gly Pro Leu
130 135 140

Ala Ala Pro Asn Leu Pro Lys Ile Lys Gly Ile Glu Thr Phe Lys Gly
145 150 155 160

Glu Leu His His Thr Ser Arg Trp Pro Lys Asp Val Thr Phe Ser Gly
165 170 175

Lys Arg Val Gly Val Ile Gly Thr Gly Ser Thr Gly Val Gln Val Ile
180 185 190

Thr Ala Ile Ala Ser Gln Val Lys His Leu Thr Val Phe Gln Arg Ser
195 200 205

Ala Gln Tyr Ser Val Pro Ile Gly Asn Val Val Met Ser Glu Thr Asp
210 215 220

Val Ala Lys Ile Lys Glu Asn Tyr Asp Gln Ile Trp Glu Asn Val Trp
225 230 235 240

Asn Ser Ala Leu Gly Phe Gly Leu Ser Glu Ser Thr Leu Pro Thr Met
245 250 255

Ser Val Ser Ala Glu Glu Arg Asp Lys Ile Phe Glu Lys Ala Trp Gln
260 265 270

Glu Gly Gly Gly Leu Arg Phe Met Phe Glu Thr Phe Gly Asp Ile Ala
275 280 285

Val Asp Glu Thr Ala Asn Ile Glu Ala Gln Asn Phe Ile Lys Lys Lys
290 295 300

```
Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 69
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 69

```
atgacccaga agatggactt tgatgcgatc attatcggcg cgggtttcgg tggcctgtac      60

agcctgaaga aactgcgtga cgattttaac ctgaaagtgc gtgcgttcga tcgtgcggcg     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtccgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720
```

aacagcgcgc tgggcttcgg tctgaacgaa agcaccctgc cgaccatgag cgttagcgcg 780
gaggaacgtg ataaaatttt tgagaaggcg tggcaggaag gtggcggtct gcgttttatg 840
ttcgagacct tcggtgacat cgcggtggat gagaccgcga acattgaagc gcaaaacttc 900
atcaagaaaa agattagcga aatcgtgaag gacccgttcg ttgcgaaaaa gctgaccccg 960
accgacctgt acgcgtgccg tccgctgtgc gatagcggct actatgagat ttttaaccgt 1020
gacaacgtga gcctggaaga tgttaaggcg aacccgattg tggagatcaa agaagactgc 1080
gtggttaccg cggatggtgt tgagcacaag ctggatatgc tgatctgcgc gaccggcttc 1140
gacgcggttg atggtaacta cattcgtatg gacatccgtg gcaaagatgg tattagcatc 1200
aaagaccact ggaaggatgg cccgaacagc tatctgggta tgatggttag caactttccg 1260
aacatgttca tggtttttgg cccgaacggt ccgctggcga acagcccgcc gatcatcgag 1320
acccaagtgc gttggattgc ggacctgatc ggctatgcgg aggatcacca gattaaccaa 1380
atcgaagcga ccaaggacgc ggttgataac tggaccaaca cctgcagcga cattgcgaac 1440
aagaccctgt ttgcgaaagc ggaaagctgg atcttcggcg cgaacgtgcc gggtaaaaag 1500
aacaccgttt acctgtatat gggcggtctg aaagagtacc gtaaccagat tagcgaagtg 1560
agcaacaaca actataaggg ttgcctgctg aaacaaagcg ttaaaaagac caacctgatc 1620
gaaagctaa 1629

<210> SEQ ID NO 70
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 70

Met Thr Gln Lys Met Asp Phe Asp Ala Ile Ile Ile Gly Ala Gly Phe
1 5 10 15

Gly Gly Leu Tyr Ser Leu Lys Lys Leu Arg Asp Asp Phe Asn Leu Lys
20 25 30

Val Arg Ala Phe Asp Arg Ala Ala Glu Val Gly Gly Thr Trp Phe Trp
35 40 45

Asn Gln Tyr Pro Gly Ala Leu Ser Asp Ser Glu Thr His Leu Tyr Cys
50 55 60

Tyr Ser Trp Asp Lys Glu Leu Leu Gln Glu Met Glu Ile Lys Arg Lys
65 70 75 80

Tyr Ile Ser Gln Pro Asp Val Leu Ala Tyr Leu Lys Arg Val Ala Asp
85 90 95

Lys His Asp Leu Arg Lys Asp Ile Gln Phe Glu Thr Gly Ile Arg Ser
100 105 110

Ala Tyr Phe Asp Glu Glu Asn Ser Phe Trp Asn Val Thr Thr Glu Asn
115 120 125

Asp Glu Lys Phe Thr Ala Arg Phe Leu Ile Thr Ala Leu Gly Pro Leu
130 135 140

Ala Ala Pro Asn Leu Pro Lys Ile Lys Gly Ile Glu Thr Phe Lys Gly
145 150 155 160

Glu Leu His His Thr Ser Arg Trp Pro Lys Asp Val Thr Phe Ser Gly
165 170 175

Lys Arg Val Gly Val Ile Gly Thr Gly Ser Thr Gly Val Gln Val Ile
180 185 190

```
Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Ser Trp Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 71
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 71

atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120
```

```
gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggcttcgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaatgccgt atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 72
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 72

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
```

```
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Phe Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Pro Gly Lys Lys Asn Thr Val Tyr Leu Tyr Met Gly Gly Leu Lys Glu
            500                 505                 510
```

```
Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 73
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 73

```
atgacccaga agatggactt tgatgcgatc attatcggcg cgggtttcgg tggcctgtac     60

agcctgaaga aactgcgtga cgattttaac ctgaaagtgc gtgcgttcga tcgtgcgacc    120

gaggttggtg gcacctggtt ttggaaccaa tatccgggtg cgctgagcga cagcgagacc    180

cacctgtact gctatagctg ggataaggaa ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccggtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggctacgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggtaacta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaatgccgt atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 74
<211> LENGTH: 542
<212> TYPE: PRT
<213> ORGANISM: Artificial Sequence
<220> FEATURE:

<223> OTHER INFORMATION: The sequence is synthesized.

<400> SEQUENCE: 74

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400
```

```
Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 75
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 75

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtccgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggctacgg tctgaacgaa agcaccctgc cgaccatgag cgttagcgcg     780

gaggaacgtg ataaaatttt tgagaaggcg tggcaggaag gtggcggtct gcgttttatg     840

ttcgagacct tcggtgacat cgcggtggat gagaccgcga acattgaagc gcaaaacttc     900

atcaagaaaa agattagcga aatcgtgaag gacccgttcg ttgcgaaaaa gctgaccccg     960

accgacctgt acgcgtgccg tccgctgtgc gatagcggct actatgagat ttttaaccgt    1020

gacaacgtga gcctggaaga tgttaaggcg aacccgattg tggagatcaa agaagactgc    1080

gtggttaccg cggatggtgt tgagcacaag ctggatatgc tgatctgcgc gaccggcttc    1140

gacgcggttg atggtaacta cattcgtatg gacatccgtg gcaaagatgg tattagcatc    1200

aaagaccact ggaaggatgg cccgaacagc tatctgggta tgatggttag caactttccg    1260
```

```
aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaatgccgt atcttcggcg cgaacgtgcc gggtaaaaag   1500

tacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 76
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 76

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
```

```
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Asn Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Pro Gly Lys Lys Tyr Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540


<210> SEQ ID NO 77
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 77

atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtccgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660
```

```
agcgagaccg acgttgcgaa aattaaggag aactatgatc aaatctggga aaacgtgtgg    720

aacagcgcgc tgggctacgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggttccta cattcgtatg gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaatgccgt atcttcggcg cgaacgtgcc gggtaaaaag   1500

tacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 78
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 78

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190
```

```
Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Ser Tyr Ile Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Pro Gly Lys Lys Tyr Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 79
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 79

```
atgacccaga agatggactt tgatgcgatc attatcggcg cgggtttcgg tggcctgtac      60
```

```
agcctgaaga aactgcgtga cgattttaac ctgaaagtgc gtgcgttcga tcgtgcgacc    120
gaggttggtg gcacctggtt ttggaaccaa tatccgggtg cgctgagcga cagcgagacc    180
cacctgtact gctatagctg ggataaggaa ctgctgcagg agatggaaat taagcgtaag    240
tacatcagcc aaccggacgt gctggcgtat ctgaaacgtg ttgcggacaa gcacgatctg    300
cgtaaagaca ttcagttcga aaccggcatc cgtagcgcgt actttgatga ggaaaacagc    360
ttctggaacg tgaccaccga gaacgacgaa aagtttaccg cgcgtttcct gatcaccgcg    420
ctgggtccgc tggcggcgcc gaacctgccg aaaattaagg gcatcgagac ctttaaaggt    480
gaactgcacc acaccagccg ttggccgaag gacgttacct tcagcggcaa acgtgtgggt    540
gttattggca ccggtagcac cggcgtgcag gttattaccg cgatcgcgag ccaagtgaaa    600
cacctgaccg tttttcagcg tagcgcgcaa tacagcgtgc cgatcggtaa cgtggttatg    660
agcgagaccg acgttgcgaa aattaaggag aactatgatc aaatctggga aaacgtgtgg    720
aacagcgcgc tgggctacgg tctgaacgaa agcaccctgc cgaccatgag cgttagcgcg    780
gaggaacgtg ataaaatttt tgagaaggcg tggcaggaag gtggcggtct gcgttttatg    840
ttcgagacct tcggtgacat cgcggtggat gagaccgcga acattgaagc gcaaaacttc    900
atcaagaaaa agattagcga aatcgtgaag gacccgttcg ttgcgaaaaa gctgaccccg    960
accgacctgt acgcgtgccg tccgctgtgc gatagcggct actatgagat ttttaaccgt   1020
gacaacgtga gcctggaaga tgttaaggcg aacccgattg tggagatcaa agaagactgc   1080
gtggttaccg cggatggtgt tgagcacaag ctggatatgc tgatctgcgc gaccggcttc   1140
gacgcggttg atggttccta ctttcgtatg gacatccgtg gcaaagatgg tattagcatc   1200
aaagaccact ggaaggatgg cccgaacagc tatctgggta tgatggttag caactttccg   1260
aacatgttca tggtttttgg cccgaacggt ccgctggcga acagcccgcc gatcatcgag   1320
acccaagtgc gttggattgc ggacctgatc ggctatgcgg aggatcacca gattaaccaa   1380
atcgaagcga ccaaggacgc ggttgataac tggaccaaca cctgcagcga cattgcgaac   1440
aagaccctgt ttgcgaaagc ggaatgccgt atcttcggcg cgaacgtgcc gggtaaaaag   1500
tacaccgttt acctgtatat gggcggtctg aaagagtacc gtaaccagat tagcgaagtg   1560
agcaacaaca actataaggg ttgcctgctg aaacaaagcg ttaaaaagac caacctgatc   1620
gaaagctaa                                                           1629
```

<210> SEQ ID NO 80
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 80

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80
```

```
Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Ser Tyr Phe Arg Met Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Pro Gly Lys Lys Tyr Thr Val Tyr Leu Tyr Met Gly Gly Leu Lys Glu
```

```
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 81
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 81

```
atgacccaga agatggactt tgatgcgatc attatcggcg cgggtttcgg tggcctgtac      60

agcctgaaga aactgcgtga cgattttaac ctgaaagtgc gtgcgttcga tcgtgcgacc     120

gaggttggtg gcacctggtt ttggaaccaa tatccgggtg cgctgagcga cagcgagacc     180

cacctgtact gctatagctg ggataaggaa ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtccgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggctacgg tctgaacgaa agcaccctgc cgaccatgag cgttagcgcg     780

gaggaacgtg ataaaatttt tgagaaggcg tggcaggaag gtggcggtct gcgttttatg     840

ttcgagacct tcggtgacat cgcggtggat gagaccgcga acattgaagc gcaaaacttc     900

atcaagaaaa agattagcga aatcgtgaag gacccgttcg ttgcgaaaaa gctgaccccg     960

accgacctgt acgcgtgccg tccgctgtgc gatagcggct actatgagat ttttaaccgt    1020

gacaacgtga gcctggaaga tgttaaggcg aacccgattg tggagatcaa agaagactgc    1080

gtggttaccg cggatggtgt tgagcacaag ctggatatgc tgatctgcgc gaccggcttc    1140

gacgcggttg atggttccta caagcgtata gacatccgtg gcaaagatgg tattagcatc    1200

aaagaccact ggaaggatgg cccgaacagc tatctgggta tgatggttag caactttccg    1260

aacatgttca tggtttttgg cccgaacggt ccgctggcga acagcccgcc gatcatcgag    1320

acccaagtgc gttggattgc ggacctgatc ggctatgcgg aggatcacca gattaaccaa    1380

atcgaagcga ccaaggacgc ggttgataac tggaccaaca cctgcagcga cattgcgaac    1440

aagaccctgt ttgcgaaagc ggaatgccgt atcttcggcg cgaacgtgcc gggtaaaaag    1500

tacaccgttt acctgtatat gggcggtctg aaagagtacc gtaaccagat tagcgaagtg    1560

agcaacaaca actataaggg ttgcctgctg aaacaaagcg ttaaaaagac caacctgatc    1620

gaaagctaa                                                            1629
```

<210> SEQ ID NO 82
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 82

```
Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Ser Tyr Lys Arg Ile Asp Ile Arg Gly Lys Asp Gly Ile Ser Ile
385                 390                 395                 400
```

```
Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Pro Gly Lys Lys Tyr Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 83
<211> LENGTH: 34
<212> TYPE: DNA
<213> ORGANISM: Artificial Sequence
<220> FEATURE:
<223> OTHER INFORMATION: The sequence is synthesized.

<400> SEQUENCE: 83
gggaattcca tatgatgacc cagaagatgg actt 34

<210> SEQ ID NO 84
<211> LENGTH: 29
<212> TYPE: DNA
<213> ORGANISM: Artificial Sequence
<220> FEATURE:
<223> OTHER INFORMATION: The sequence is synthesized.

<400> SEQUENCE: 84
cccaagcttt tagctttcga tcaggttgg 29

<210> SEQ ID NO 85
<211> LENGTH: 33
<212> TYPE: DNA
<213> ORGANISM: Artificial Sequence
<220> FEATURE:
<223> OTHER INFORMATION: The sequence is synthesized.

<400> SEQUENCE: 85
accgacctgt acgcgtgccg tccgctgtgc gat 33

<210> SEQ ID NO 86
<211> LENGTH: 33
<212> TYPE: DNA
<213> ORGANISM: Artificial Sequence
<220> FEATURE:
<223> OTHER INFORMATION: The sequence is synthesized.

<400> SEQUENCE: 86
atcgcacagc ggacggcacg cgtacaggtc ggt 33

<210> SEQ ID NO 87
<211> LENGTH: 33

<212> TYPE: DNA
<213> ORGANISM: Artificial Sequence
<220> FEATURE:
<223> OTHER INFORMATION: The sequence is synthesized.

<400> SEQUENCE: 87
ggcccgaacg gtccgctgac caacctgccg ccg 33

<210> SEQ ID NO 88
<211> LENGTH: 33
<212> TYPE: DNA
<213> ORGANISM: Artificial Sequence
<220> FEATURE:
<223> OTHER INFORMATION: The sequence is synthesized.

<400> SEQUENCE: 88
cggcggcagg ttggtcagcg gaccgttcgg gcc 33

<210> SEQ ID NO 89
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 89
atgacccaga agatggactt tgatgcgatc attatcggcg cgggtttcgg tggcctgtac 60
agcctgaaga aactgcgtga cgattttaac ctgaaagtgc gtgcgttcga tcgtgcgacc 120
gaggttggtg gcacctggtt ttggaaccaa tatccgggtg cgctgagcga cagcgagacc 180
cacctgtact gctatagctg ggataaggaa ctgctgcagg agatggaaat taagcgtaag 240
tacatcagcc aaccggacgt gctggcgtat ctgaaacgtg ttgcggacaa gcacgatctg 300
cgtaaagaca ttcagttcga aaccggcatc cgtagcgcgt actttgatga ggaaaacagc 360
ttctggaacg tgaccaccga gaacgacgaa aagtttaccg cgcgtttcct gatcaccgcg 420
ctgggtccgc tggcggcgcc gaacctgccg aaaattaagg gcatcgagac ctttaaaggt 480
gaactgcacc acaccagccg ttggccgaag gacgttacct tcagcggcaa acgtgtgggt 540
gttattggca ccggtagcac cggcgtgcag gttattaccg cgatcgcgag ccaagtgaaa 600
cacctgaccg tttttcagcg tagcgcgcaa tacagcgtgc cgatcggtaa cgtggttatg 660
agcgagaccg acgttgcgaa aattaaggag aactatgatc aaatctggga aaacgtgtgg 720
aacagcgcgc tgggctacgg tctgaacgaa agcaccctgc cgaccatgag cgttagcgcg 780
gaggaacgtg ataaaatttt tgagaaggcg tggcaggaag gtggcggtct gcgttttatg 840
ttcgagacct tcggtgacat cgcggtggat gagaccgcga acattgaagc gcaaaacttc 900
atcaagaaaa agattagcga aatcgtgaag gacccgttcg ttgcgaaaaa gctgaccccg 960
accgacctgt acgcgtgccg tccgctgtgc gatagcggct actatgagat ttttaaccgt 1020
gacaacgtga gcctggaaga tgttaaggcg aacccgattg tggagatcaa agaagactgc 1080
gtggttaccg cggatggtgt tgagcacaag ctggatatgc tgatctgcgc gaccggcttc 1140
gacgcggttg atggttccta caagcgtata gacatccgtg gcaaagatgg tattagcatc 1200
aaagaccact ggaaggatgg cccgaacagc tatctgggta tgatggttag caactttccg 1260
aacatgttca tggtttttgg cccgaacggt ccgctggcga acagcccgcc gatcatcgag 1320
acccaagtgc gttggattgc ggacctgatc ggctatgcgg aggatcacca gattaaccaa 1380
atcgaagcga ccaaggacgc ggttgataac tggaccaaca cctgcagcga cattgcgaac 1440

```
aagaccctgt ttgcgaaagc gaaatgccgt atcttcggcg cgaacgtgcc gggtaaaaag   1500

aacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

```
<210> SEQ ID NO 90
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 90

Met Thr Gln Lys Met Asp Phe Asp Ala Ile Ile Ile Gly Ala Gly Phe
1               5                   10                  15

Gly Gly Leu Tyr Ser Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Leu Ser Asp Ser Glu Thr His Leu Tyr Cys
    50                  55                  60

Tyr Ser Trp Asp Lys Glu Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
```

```
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Ser Tyr Lys Arg Ile Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Lys Cys Arg Ile Phe Gly Ala Asn Val
                485                 490                 495

Pro Gly Lys Lys Asn Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 91
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 91

```
atgacccaga agatggactt tgatgcgatc attatcggcg cgggtttcgg tggcctgtac      60

ggcctgaaga aactgcgtga cgattttaac ctgaaagtgc gtgcgttcga tcgtgcgacc     120

gaggttggtg gcacctggtt ttggaaccaa tatccgggtg cgtatagcga cagcgagacc     180

cacctgtact gctatagctg ggataaggga ctgctgcagg agatggaaat taagcgtaag     240

tacatcagcc aaccggacgt gctggcgtat ctgaaacgtg ttgcggacaa gcacgatctg     300

cgtaaagaca ttcagttcga aaccggcatc cgtagcgcgt actttgatga ggaaaacagc     360

ttctggaacg tgaccaccga gaacgacgaa aagtttaccg cgcgtttcct gatcaccgcg     420

ctgggtccgc tggcggcgcc gaacctgccg aaaattaagg gcatcgagac ctttaaaggt     480

gaactgcacc acaccagccg ttggccgaag gacgttacct tcagcggcaa acgtgtgggt     540

gttattggca ccggtagcac cggcgtgcag gttattaccg cgatcgcgag ccaagtgaaa     600

cacctgaccg tttttcagcg tagcgcgcaa tacagcgtgc cgatcggtaa cgtggttatg     660

agcgagaccg acgttgcgaa aattaaggag aactatgatc aaatctggga aaacgtgtgg     720

aacagcgcgc tgggctacgg tctgaacgaa agcaccctgc cgaccatgag cgttagcgcg     780

gaggaacgtg ataaaatttt tgagaaggcg tggcaggaag gtggcggtct gcgttttatg     840
```

```
ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggttccta caagcgtata gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaatgccgt atcttcggcg cgaacgtgcc gggtaaaaag   1500

tacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 92
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 92

```
Met Thr Gln Lys Met Asp Phe Asp Ala Ile Ile Ile Gly Ala Gly Phe
1               5                   10                  15

Gly Gly Leu Tyr Gly Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Tyr Ser Asp Ser Glu Thr His Leu Tyr Cys
    50                  55                  60

Tyr Ser Trp Asp Lys Gly Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Gly Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220
```

```
Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Ser Tyr Lys Arg Ile Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Pro Gly Lys Lys Tyr Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 93
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 93

```
atgacccaga agatggactt tgatgcgatc attatcggcg cgggtttcgg tggcctgtac      60

ggcctgaaga aactgcgtga cgattttaac ctgaaagtgc gtgcgttcga tcgtgcgacc     120

gaggttggtg gcacctggtt ttggaaccaa tatccgggtg cgtatagcga cagcgagacc     180

cacctgtact gctatagctg ggataaggga ctgctgcagg agatggaaat taagcgtaag     240
```

```
tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tggcggcgcc gaacctgccg aaaattaagg gcatcgagac ctttaaaggt    480

gaactgcacc acaccagccg ttggccgaag gacgttacct tcagcggcaa acgtgtgggt    540

gttattggca ccagtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggctacgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggttccta caagcgtata gacatccgtg gcaaagatgg tattagcatc   1200

aaagaccact ggaaggatgg cccgaacagc tatctgggta tgatggttag caactttccg   1260

aacatgttca tggtttttgg cccgaacggt ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440

aagaccctgt ttgcgaaagc ggaatgccgt atcttcggcg cgaacgtgag cggtaaaaag   1500

tacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

<210> SEQ ID NO 94
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 94

```
Met Thr Gln Lys Met Asp Phe Asp Ala Ile Ile Ile Gly Ala Gly Phe
1               5                   10                  15

Gly Gly Leu Tyr Gly Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Tyr Ser Asp Ser Glu Thr His Leu Tyr Cys
    50                  55                  60

Tyr Ser Trp Asp Lys Gly Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110
```

```
Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ala Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Ser Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Ser Tyr Lys Arg Ile Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Ser Gly Lys Lys Tyr Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
```

530 535 540

<210> SEQ ID NO 95
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 95
atgacccaga agatggactt tgatgcgatc attatcggcg cgggtttcgg tggcctgtac 60
ggcctgaaga aactgcgtga cgattttaac ctgaaagtgc gtgcgttcga tcgtgcgacc 120
gaggttggtg gcacctggtt ttggaaccaa tatccgggtg cgtatagcga cagcgagacc 180
cacctgtact gctatagctg ggataaggga ctgctgcagg agatggaaat taagcgtaag 240
tacatcagcc aaccggacgt gctggcgtat ctgaaacgtg ttgcggacaa gcacgatctg 300
cgtaaagaca ttcagttcga aaccggcatc cgtagcgcgt actttgatga ggaaaacagc 360
ttctggaacg tgaccaccga gaacgacgaa aagtttaccg cgcgtttcct gatcaccgcg 420
ctgggtccgc tgagcgcgcc gaacctgccg aaaattaagg gcatcgagac ctttaaaggt 480
gaactgcacc acaccagccg ttggccgaag gacgttacct tcagcggcaa acgtgtgggt 540
gttattggca ccagtagcac cggcgtgcag gttattaccg cgatcgcgag ccaagtgaaa 600
cacctgaccg tttttcagcg tagcgcgcaa tacagcgtgc cgatcggtaa cgtggttatg 660
agcgagaccg acgttgcgaa aattaaggag aactatgatc aaatctggga aaacgtgtgg 720
aacagcgcgc tgggctacgg tctgaacgaa agcaccctgc cgaccatgag cgttagcgcg 780
gaggaacgtg ataaaatttt tgagaaggcg tggcaggaag gtggcggtct gcgttttatg 840
ttcgagacct tcggtgacat cgcggtggat gagaccgcga acattgaagc gcaaaacttc 900
atcaagaaaa agattagcga aatcgtgaag gacccgttcg ttgcgaaaaa gctgaccccg 960
accgacctgt acgcgtgccg tccgctgtgc gatagcggct actatgagat ttttaaccgt 1020
gacaacgtga gcctggaaga tgttaaggcg aacccgattg tggagatcaa agaagactgc 1080
gtggttaccg cggatggtgt tgagcacaag ctggatatgc tgatctgcgc gaccggcttc 1140
gacgcggttg atggttccta caagcgtata gacatccgtg gcaaagatgg tattagcatc 1200
aaagaccact ggaaggatgg cccgaacagc tatctgggta tgatggttag caactttccg 1260
aacatgttca tggtttttgg cccgaacggt ccgctggcga acagcccgcc gatcatcgag 1320
acccaagtgc gttggattgc ggacctgatc ggctatgcgg aggatcacca gattaaccaa 1380
atcgaagcga ccaaggacgc ggttgataac tggaccaaca cctgcagcga cattgcgaac 1440
aagaccctgt ttgcgaaagc ggaatgccgt atcttcggcg cgaacgtgag cggtaaaaag 1500
tacaccgttt acctgtatat gggcggtctg aaagagtacc gtaaccagat tagcgaagtg 1560
agcaacaaca actataaggg ttgcctgctg aaacaaagcg ttaaaaagac caacctgatc 1620
gaaagctaa 1629

<210> SEQ ID NO 96
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 96

Met Thr Gln Lys Met Asp Phe Asp Ala Ile Ile Ile Gly Ala Gly Phe

-continued

```
1               5                   10                  15

Gly Gly Leu Tyr Gly Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Tyr Ser Asp Ser Glu Thr His Leu Tyr Cys
    50                  55                  60

Tyr Ser Trp Asp Lys Gly Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ser Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Ser Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320

Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Ser Tyr Lys Arg Ile Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Gly Pro Leu
            420                 425                 430
```

```
Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Ser Gly Lys Lys Tyr Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

<210> SEQ ID NO 97
<211> LENGTH: 1629
<212> TYPE: DNA
<213> ORGANISM: Artificial Sequence
<220> FEATURE:
<223> OTHER INFORMATION: The sequence is synthesized.

<400> SEQUENCE: 97

```
atgacccaga agatggactt tgatgcgatc attatcggcg cgggtttcgg tggcctgtac     60

ggcctgaaga aactgcgtga cgattttaac ctgaaagtgc gtgcgttcga tcgtgcgacc    120

gaggttggtg gcacctggtt ttggaaccaa tatccgggtg cgtatagcga cagcgagacc    180

cacctgtact gctatagctg ggataaggga ctgctgcagg agatggaaat taagcgtaag    240

tacatcagcc aaccggacgt gctggcgtat ctgaaacgtg ttgcggacaa gcacgatctg    300

cgtaaagaca ttcagttcga aaccggcatc cgtagcgcgt actttgatga ggaaaacagc    360

ttctggaacg tgaccaccga gaacgacgaa aagtttaccg cgcgtttcct gatcaccgcg    420

ctgggtccgc tgagcgcgcc gaacctgccg aaaattaagg gcatcgagac ctttaaaggt    480

gaactgcacc acaccagccg ttggccgaag gacgttacct tcagcggcaa acgtgtgggt    540

gttattggca ccagtagcac cggcgtgcag gttattaccg cgatcgcgag ccaagtgaaa    600

cacctgaccg tttttcagcg tagcgcgcaa tacagcgtgc cgatcggtaa cgtggttatg    660

agcgagaccg acgttgcgaa aattaaggag aactatgatc aaatctggga aaacgtgtgg    720

aacagcgcgc tgggctacgg tctgaacgaa agcaccctgc cgaccatgag cgttagcgcg    780

gaggaacgtg ataaaatttt tgagaaggcg tggcaggaag gtggcggtct gcgttttatg    840

ttcgagacct tcggtgacat cgcggtggat gagaccgcga acattgaagc gcaaaacttc    900

atcaagaaaa agattagcga aatcgtgaag gacccgttcg ttgcgaaaaa gctgaccccg    960

accgacctgt acgcgtgccg tccgctgtgc gatagcggct actatgagat ttttaaccgt   1020

gacaacgtga gcctggaaga tgttaaggcg aacccgattg tggagatcaa agaagactgc   1080

gtggttaccg cggatggtgt tgagcacaag ctggatatgc tgatctgcgc gaccggcttc   1140

gacgcggttg atggttccta caagcgtata gacatccgtg gcaaagatgg tattagcatc   1200

aaagaccact ggaaggatgg cccgaacagc tatctgggta tgatggttag caactttccg   1260

aacatgttca tggtttttgg cccgaacacc ccgctggcga acagcccgcc gatcatcgag   1320

acccaagtgc gttggattgc ggacctgatc ggctatgcgg aggatcacca gattaaccaa   1380

atcgaagcga ccaaggacgc ggttgataac tggaccaaca cctgcagcga cattgcgaac   1440
```

```
aagaccctgt ttgcgaaagc ggaatgccgt atcttcggcg cgaacgtgag cggtaaaaag   1500

tacaccgttt acctgtatat gggcggtctg aaagagtacc gtaaccagat tagcgaagtg   1560

agcaacaaca actataaggg ttgcctgctg aaacaaagcg ttaaaaagac caacctgatc   1620

gaaagctaa                                                           1629
```

```
<210> SEQ ID NO 98
<211> LENGTH: 542
<212> TYPE: PRT
<213> ORGANISM: Artificial Sequence
<220> FEATURE:
<223> OTHER INFORMATION: The sequence is synthesized.

<400> SEQUENCE: 98

Met Thr Gln Lys Met Asp Phe Asp Ala Ile Ile Ile Gly Ala Gly Phe
1               5                   10                  15

Gly Gly Leu Tyr Gly Leu Lys Lys Leu Arg Asp Asp Phe Asn Leu Lys
            20                  25                  30

Val Arg Ala Phe Asp Arg Ala Thr Glu Val Gly Gly Thr Trp Phe Trp
        35                  40                  45

Asn Gln Tyr Pro Gly Ala Tyr Ser Asp Ser Glu Thr His Leu Tyr Cys
    50                  55                  60

Tyr Ser Trp Asp Lys Gly Leu Leu Gln Glu Met Glu Ile Lys Arg Lys
65                  70                  75                  80

Tyr Ile Ser Gln Pro Asp Val Leu Ala Tyr Leu Lys Arg Val Ala Asp
                85                  90                  95

Lys His Asp Leu Arg Lys Asp Ile Gln Phe Glu Thr Gly Ile Arg Ser
            100                 105                 110

Ala Tyr Phe Asp Glu Glu Asn Ser Phe Trp Asn Val Thr Thr Glu Asn
        115                 120                 125

Asp Glu Lys Phe Thr Ala Arg Phe Leu Ile Thr Ala Leu Gly Pro Leu
    130                 135                 140

Ser Ala Pro Asn Leu Pro Lys Ile Lys Gly Ile Glu Thr Phe Lys Gly
145                 150                 155                 160

Glu Leu His His Thr Ser Arg Trp Pro Lys Asp Val Thr Phe Ser Gly
                165                 170                 175

Lys Arg Val Gly Val Ile Gly Thr Ser Ser Thr Gly Val Gln Val Ile
            180                 185                 190

Thr Ala Ile Ala Ser Gln Val Lys His Leu Thr Val Phe Gln Arg Ser
        195                 200                 205

Ala Gln Tyr Ser Val Pro Ile Gly Asn Val Val Met Ser Glu Thr Asp
    210                 215                 220

Val Ala Lys Ile Lys Glu Asn Tyr Asp Gln Ile Trp Glu Asn Val Trp
225                 230                 235                 240

Asn Ser Ala Leu Gly Tyr Gly Leu Asn Glu Ser Thr Leu Pro Thr Met
                245                 250                 255

Ser Val Ser Ala Glu Glu Arg Asp Lys Ile Phe Glu Lys Ala Trp Gln
            260                 265                 270

Glu Gly Gly Gly Leu Arg Phe Met Phe Glu Thr Phe Gly Asp Ile Ala
        275                 280                 285

Val Asp Glu Thr Ala Asn Ile Glu Ala Gln Asn Phe Ile Lys Lys Lys
    290                 295                 300

Ile Ser Glu Ile Val Lys Asp Pro Phe Val Ala Lys Lys Leu Thr Pro
305                 310                 315                 320
```

-continued

```
Thr Asp Leu Tyr Ala Cys Arg Pro Leu Cys Asp Ser Gly Tyr Tyr Glu
                325                 330                 335

Ile Phe Asn Arg Asp Asn Val Ser Leu Glu Asp Val Lys Ala Asn Pro
            340                 345                 350

Ile Val Glu Ile Lys Glu Asp Cys Val Val Thr Ala Asp Gly Val Glu
        355                 360                 365

His Lys Leu Asp Met Leu Ile Cys Ala Thr Gly Phe Asp Ala Val Asp
    370                 375                 380

Gly Ser Tyr Lys Arg Ile Asp Ile Arg Gly Lys Asp Gly Ile Ser Ile
385                 390                 395                 400

Lys Asp His Trp Lys Asp Gly Pro Asn Ser Tyr Leu Gly Met Met Val
                405                 410                 415

Ser Asn Phe Pro Asn Met Phe Met Val Phe Gly Pro Asn Thr Pro Leu
            420                 425                 430

Ala Asn Ser Pro Pro Ile Ile Glu Thr Gln Val Arg Trp Ile Ala Asp
        435                 440                 445

Leu Ile Gly Tyr Ala Glu Asp His Gln Ile Asn Gln Ile Glu Ala Thr
    450                 455                 460

Lys Asp Ala Val Asp Asn Trp Thr Asn Thr Cys Ser Asp Ile Ala Asn
465                 470                 475                 480

Lys Thr Leu Phe Ala Lys Ala Glu Cys Arg Ile Phe Gly Ala Asn Val
                485                 490                 495

Ser Gly Lys Lys Tyr Thr Val Tyr Leu Tyr Met Gly Gly Leu Lys Glu
            500                 505                 510

Tyr Arg Asn Gln Ile Ser Glu Val Ser Asn Asn Asn Tyr Lys Gly Cys
        515                 520                 525

Leu Leu Lys Gln Ser Val Lys Lys Thr Asn Leu Ile Glu Ser
    530                 535                 540
```

MONOOXYGENASE AND USE IN PREPARATION OF OPTICALLY PURE SULFOXIDE

CROSS REFERENCE TO THE RELATED APPLICATIONS

This application is the national phase entry of International Application No. PCT/CN2019/120798, filed on Nov. 26, 2019, which is based upon and claims priority to Chinese Patent Application No. 201811420321.1, filed on Nov. 26, 2018, the entire contents of which are incorporated herein by reference.

TECHNICAL FIELD

The present invention relates to a non-naturally occurring thioether monooxygenase and its use in enzymatically catalyzing the asymmetric oxidation of a thioether-based compound to prepare a sulfoxide compound.

BACKGROUND

Esomeprazole, also known as (S)-omeprazole, with a chemical name of 5-methoxy-2-((9-((4-methoxy-3,5-dimethyl-2-pyridyl)methyl)sulfinyl)-1H-benzimidazole, has a chemical structure shown in Formula I. Esomeprazole is the single (9-configuration isomer of omeprazole that is the first clinical proton pump inhibitor. This drug is mainly used to treat duodenal ulcer, gastric ulcer, gastritis and digestive esophagitis. It has been clinically proven that this drug has lower toxic side effects and better therapeutic effects than the racemate and (R)-Omeprazole. Esomeprazole is chemically synthesized via asymmetric oxidation of thioether by using metallic catalysts, but such methods have such shortcomings as limited optical purity, excessive oxidation, many by-products, complicated isolation and purification processes, and the like.

Formula I

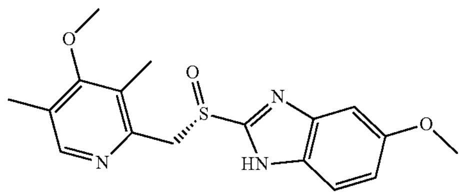

Thioethers are subject to enzymatic asymmetric oxidation to produce a single enantiomer of the chiral sulfoxide. Such a method has low environmental pollution, few by-products, good atom economy, and high optical purity of the product, and therefore, the synthesis of chiral sulfoxide by enzymatic asymmetric oxidation has received more and more attentions.

The inventor has screened and obtained a strain of *Rhodococcus* (CGMCC2547) that can catalyze the asymmetric oxidation of a series of prochiral phenylalkyl thioethers and their derivatives to produce optically active chiral benzyl sulfoxides and their derivatives (see CN101372676B). Czechic scientists have screened and obtained a strain of *Bacillus pumilus Lysinibacillus* sp. of which the growing cells can be used to catalyze the synthesis of (S)-omeprazole from omeprazole thioether. However, when the substrate is at a concentration of only 0.1 g/L, the conversion rate is only 43% after 44 hours (*Bioresources Technology* 2011, 102: 7621-7626). In the patent WO2011071982, a directed evolution was performed on the cyclohexanone monooxygenase NCIMB9871, wherein the engineered enzyme catalyzed 100 g/L substrate loading capacity; lyophilized enzyme powder was added at 10 g/L in 5 batches; and the substrate was transformed at 69 hours after reaction with an ee value of up to 99%. On the basis of the mutation sequence 157 published in the patent WO2011071982, the patent CN108118035A discloses a mutant with a catalytic substrate concentration of up to 165 g/L, wherein the mutant is obtained by mutating the serine at position 386 of the mutant 157 to asparagine, and the serine at position 435 of the mutant 157 to threonine. Although these can achieve the synthesis of esomeprazole by the asymmetric oxidation of omeprazole thioether, there are still such shortcomings as low catalytic activity, high catalyst amount, low reaction scale limited to laboratory level.

SUMMARY

The present invention provides a monooxygenase including a mutant with an amino acid sequence shown in SEQ ID NO:2, wherein the mutations of the mutant include replacements of amino acid residues at specified positions selected from the following positions: Xaa21, Xaa40, Xaa55, Xaa70, Xaa143, Xaa145, Xaa156, Xaa185, Xaa220, Xaa244, Xaa246, Xaa248, Xaa249, Xaa277, Xaa281, Xaa326, Xaa386, Xaa388, Xaa390, Xaa405, Xaa426, Xaa430, Xaa432, Xaa433, Xaa435, Xaa438, Xaa465, Xaa468, Xaa488, Xaa489, Xaa490, Xaa497, Xaa501 and Xaa505 of the amino acid sequence shown in SEQ ID NO: 2.

In an embodiment, the replacement of amino acid residues at the specified positions includes replacements of amino acid residues at at least 2 specified positions.

In one of the embodiments, the monooxygenase can optionally include any one or more mutations selected from the group consisting of:

(a) replacements of amino acid residue(s) at any 1, 2, 3, 4, or 5 positions other than the specified positions;

(b) deletion of amino acid residue(s) at any 1, 2, 3, 4, or 5 positions other than the specified positions; and (c) insertion of amino acid residue(s) at any 1, 2, 3, 4, or 5 positions other than the specified positions.

In one of the embodiments, the replacements of amino acid residues at the specified positions include any one or more of the following replacements:

at Xaa21, S is replaced with G; at Xaa40, T is replaced with A; at Xaa55, L is replaced with Y, W, F or N; at Xaa70, E is replaced with G; at Xaa143, L is replaced with P or A; at Xaa145, A is replaced with S; at Xaa156, E is replaced with G; at Xaa185, G is replaced with A or S; at Xaa220, M is replaced with R; at Xaa244, L is replaced with V or I; at Xaa246, F is replaced with Y; at Xaa248, L is replaced with E, N, A or W; at Xaa249, N is replaced with S; at Xaa277, F is replaced with L, V, Y, I or D; at Xaa281, F is replaced with V or A; at Xaa326, K is replaced with C or F; at Xaa386, N is replaced with S; at Xaa388, I is replaced with F, C, K, G; at Xaa390, M is replaced with S, V, I; at Xaa405, K is replaced with M; at Xaa426, L is replaced with F or P; at Xaa430, G is replaced with T or S; at Xaa432, F is replaced with L or I; at Xaa433, T is replaced with C or A; at Xaa435, L is replaced with S; at Xaa438, S is replaced with I; at Xaa465, K is replaced with R; at Xaa468, V is replaced with A; at Xaa488, E is replaced with K; at Xaa489, S is replaced with C; at Xaa490, W is replaced with R; at Xaa497, P is replaced with S; at Xaa501, N is replaced with Y; and at Xaa505, F is replaced with L.

In one of the embodiments, the replacement of amino acid residues at the specified positions includes any of the following replacements:

(1) 2 replacements, wherein at Xaa326, K is replaced with C; at Xaa432, F is replaced with L;

(2) 2 replacements, wherein at Xaa326, K is replaced with F; at Xaa432, F is replaced with L; (3) 2 replacements, wherein at Xaa326, K is replaced with C; at Xaa432, F is replaced with I;

(4) 4 replacements, wherein at Xaa326, K is replaced with C; at Xaa432, F is replaced with L; at Xaa435, L is replaced with S; at Xaa438, S is replaced with I;

(5) 4 replacements, wherein at Xaa326, K is replaced with F; at Xaa432, F is replaced with L; at Xaa435, L is replaced with S; at Xaa438, S is replaced with I;

(6) 5 replacements, wherein at Xaa326, K is replaced with C; at Xaa432, F is replaced with L; at Xaa433, T is replaced with C; at Xaa435, L is replaced with S; at Xaa438, S is replaced with I;

(7) 5 replacements, wherein at Xaa326, K is replaced with C; at Xaa432, F is replaced with L; at Xaa433, T is replaced with A; at Xaa435, L is replaced with S; at Xaa438, S is replaced with I;

(8) 6 replacements, wherein at Xaa326, K is replaced with C; at Xaa426, L is replaced with F; at Xaa432, F is replaced with L; at Xaa433, T is replaced with A; at Xaa435, L is replaced with S; at Xaa438, S is replaced with I;

(9) 6 replacements, wherein at Xaa326, K is replaced with C; at Xaa426, L is replaced with P; at Xaa432, F is replaced with L; at Xaa433, T is replaced with A; at Xaa435, L is replaced with S; at Xaa438, S is replaced with I;

(10) 7 replacements, wherein at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(11) 8 replacements, wherein at Xaa143, L is replaced with P; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(12) 8 replacements, wherein at Xaa143, L is replaced with A; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(13) 8 replacements, wherein at Xaa244, L is replaced with V; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(14) 8 replacements, wherein at Xaa244, L is replaced with I; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(15) 9 replacements, wherein at Xaa143, L is replaced with P; at Xaa248, L is replaced with E; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(16) 8 replacements, wherein at Xaa248, L is replaced with N; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(17) 8 replacements, wherein at Xaa248, L is replaced with A; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(18) 8 replacements, wherein at Xaa248, L is replaced with W; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(19) 9 replacements, wherein at Xaa143, L is replaced with P; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(20) 9 replacements, wherein at Xaa143, L is replaced with P; at Xaa277, F is replaced with V; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(21) 9 replacements, wherein at Xaa143, L is replaced with P; at Xaa277, F is replaced with Y; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(22) 8 replacements, wherein at Xaa277, F is replaced with I; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(23) 8 replacements, wherein at Xaa277, F is replaced with D; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(24) 8 replacements, wherein at Xaa281, F is replaced with V; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(25) 8 replacements, wherein at Xaa281, F is replaced with A; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(26) 10 replacements, wherein at Xaa143, L is replaced with P; at Xaa277, F is replaced with L; at Xaa281, F is replaced with V; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(27) 10 replacements, wherein at Xaa143, L is replaced with P; at Xaa277, F is replaced with V; at Xaa281, F is replaced with A; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(28) 11 replacements, wherein at Xaa143, L is replaced with P; at Xaa200, M is replaced with R; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa465, K is replaced with R; at Xaa505, F is replaced with L;

(29) 10 replacements, wherein at Xaa143, L is replaced with P; at Xaa185, G is replaced with A; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(30) 10 replacements, wherein at Xaa143, L is replaced with P; at Xaa246, F is replaced with Y; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(31) 11 replacements, wherein at Xaa143, L is replaced with P; at Xaa277, F is replaced with L; at Xaa326, K is replaced with C; at Xaa405, K is replaced with M; at Xaa426, L is replaced with F; at Xaa432, F is replaced with L; at Xaa433, T is replaced with A; at Xaa435, L is replaced with S; at Xaa438, S is replaced with I; at Xaa501, N is replaced with Y; at Xaa505, F is replaced with L;

(32) 10 replacements, wherein at Xaa143, L is replaced with P; at Xaa156, E is replaced with G; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(33) 10 replacements, wherein at Xaa143, L is replaced with P; at Xaa249, N is replaced with S; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(34) 10 replacements, wherein at Xaa40, T is replaced with A; at Xaa143, L is replaced with P; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa505, F is replaced with L;

(35) 11 replacements, wherein at Xaa143, L is replaced with P; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa505, F is replaced with L;

(36) 12 replacements, wherein at Xaa143, L is replaced with P; at Xaa246, F is replaced with Y; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa505, F is replaced with L;

(37) 13 replacements, wherein at Xaa143, L is replaced with P; at Xaa246, F is replaced with Y; at Xaa277, F is replaced with L; at Xaa326, K is replaced with C; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa501, N is replaced with Y; at Xaa505, F is replaced with L;

(38) 14 replacements, wherein at Xaa143, L is replaced with P; at Xaa246, F is replaced with Y; at Xaa277, F is replaced with L; at Xaa326, K is replaced with C; at Xaa386, N is replaced with S; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa501, N is replaced with Y; at Xaa505, F is replaced with L;

(39) 15 replacements, wherein at Xaa143, L is replaced with P; at Xaa246, F is replaced with Y; at Xaa277, F is replaced with L; at Xaa326, K is replaced with C; at Xaa386, N is replaced with S; at Xaa388, I is replaced with F; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa501, N is replaced with Y; at Xaa505, F is replaced with L;

(40) 16 replacements, wherein at Xaa143, L is replaced with P; at Xaa246, F is replaced with Y; at Xaa277, F is replaced with L; at Xaa326, K is replaced with C; at Xaa386, N is replaced with S; at Xaa388, I is replaced with K; at Xaa390, M is replaced with I; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa501, N is replaced with Y; at Xaa505, F is replaced with L;

(41) 16 replacements, wherein at Xaa143, L is replaced with P; at Xaa246, F is replaced with Y; at Xaa277, F is replaced with L; at Xaa326, K is replaced with C; at Xaa386, N is replaced with S; at Xaa388, I is replaced with K; at Xaa390, M is replaced with I; at Xaa426, L is replaced with F; at Xaa432, F is replaced with L; at Xaa433, T is replaced with A; at Xaa435, L is replaced with S; at Xaa438, S is replaced with I; at Xaa488, E is replaced with K; at Xaa489, S is replaced with C; at Xaa490, W is replaced with R; at Xaa505, F is replaced with L;

(42) 19 replacements, wherein at Xaa21, S is replaced with G; at Xaa55, L is replaced with Y; at Xaa70, E is replaced with G; at Xaa143, L is replaced with P; at Xaa246, F is replaced with Y; at Xaa277, F is replaced with L; at Xaa326, K is replaced with C; at Xaa386, N is replaced with S; at Xaa388, I is replaced with K; at Xaa390, M is replaced with I; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa501, N is replaced with Y; at Xaa505, F is replaced with L;

(43) 21 replacements, wherein at Xaa21, S is replaced with G; at Xaa55, L is replaced with Y; at Xaa70, E is replaced with G; at Xaa143, L is replaced with P; at Xaa185, G is replaced with S; at Xaa246, F is replaced with Y; at Xaa277, F is replaced with L; at Xaa326, K is replaced with C; at Xaa386, N is replaced with S; at Xaa388, I is replaced with K; at Xaa390, M is replaced with I; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa497, P is replaced with S; at Xaa501, N is replaced with Y; at Xaa505, F is replaced with L;

(44) 22 replacements, wherein at Xaa21, S is replaced with G; at Xaa55, L is replaced with Y; at Xaa70, E is replaced with G; at Xaa143, L is replaced with P; at Xaa145, A is replaced with S; at Xaa185, G is replaced with S; at Xaa246, F is replaced with Y; at Xaa277, F is replaced with L; at Xaa326, K is replaced with C; at Xaa386, N is replaced with S; at Xaa388, I is replaced with K; at Xaa390, M is replaced with I; at Xaa426, L is replaced with F; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa497, P is replaced with S; at Xaa501, N is replaced with Y; at Xaa505, F is replaced with L;

(45) 23 replacements, wherein at Xaa21, S is replaced with G; at Xaa55, L is replaced with Y; at Xaa70, E is replaced with G; at Xaa143, L is replaced with P; at Xaa145, A is replaced with S; at Xaa185, G is replaced with S; at Xaa246, F is replaced with Y; at Xaa277, F is replaced with L; at Xaa326, K is replaced with C; at Xaa386, N is replaced with S; at Xaa388, I is replaced with K; at Xaa390, M is replaced with I; at Xaa426, L is replaced with F; at Xaa430, G is replaced with T; at Xaa432, F is replaced with L; at Xaa433, T is replaced with A; at Xaa435, L is replaced with S; at Xaa438, S is replaced with I; at Xaa489, S is replaced with C; at Xaa490, W is replaced with R; at Xaa497, P is replaced with S; at Xaa501, N is replaced with Y; at Xaa505, F is replaced with L.

The present invention further provides a monooxygenase with an amino acid sequence: shown in SEQ ID NO:4, or shown in SEQ ID NO:6, or shown in SEQ ID NO:8, or shown in SEQ ID NO:10, or shown in SEQ ID NO:12, or shown in SEQ ID NO:14, or shown in SEQ ID NO:16, or shown in SEQ ID NO:18, or shown in SEQ ID NO:20, or shown in SEQ ID NO:22, or shown in SEQ ID NO:24, or shown in SEQ ID NO:26, or shown in SEQ ID NO:28, or shown in SEQ ID NO:30, or shown in SEQ ID NO:32, or shown in SEQ ID NO:34, or shown in SEQ ID NO:36, or shown in SEQ ID NO:38, or shown in SEQ ID NO:40, or shown in SEQ ID NO:42, or shown in SEQ ID NO:44, or shown in SEQ ID NO:46, or shown in SEQ ID NO:48, or shown in SEQ ID NO:50, or shown in SEQ ID NO:52, or shown in SEQ ID NO:54, or shown in SEQ ID NO:56, or shown in SEQ ID NO:58, or shown in SEQ ID NO:60, or shown in SEQ ID NO:62, or shown in SEQ ID NO:64, or shown in SEQ ID NO:66, or shown in SEQ ID NO:68, or shown in SEQ ID NO:70, or shown in SEQ ID NO:72, or shown in SEQ ID NO:74, or shown in SEQ ID NO:76, or shown in SEQ ID NO:78, or shown in SEQ ID NO:80, or shown in SEQ ID NO:82, or shown in SEQ ID NO:90, or shown in SEQ ID NO:92, or shown in SEQ ID NO:94, or shown in SEQ ID NO:96, or shown in SEQ ID NO:98.

The present invention further provides an isolated nucleic acid, and the nucleic acid encodes the above monooxygenase.

The present invention further provides a recombinant expression vector including the above-described nucleic acid.

The present invention provides a recombinant expression transformant including the above-described recombinant expression vector.

The present invention further provides a method of preparing the above-described monooxygenase, including the steps of culturing the above-described recombinant expression transformant, and isolating the monooxygenase therefrom.

The present invention further provides use of the above-described monooxygenase in asymmetric catalytic oxidation of a prochiral thioether compound to a sulfoxide compound.

In one of the embodiments, the prochiral thioether compound is selected from the group consisting of compounds as represented by any one of the following formulae:

Formula IIIa

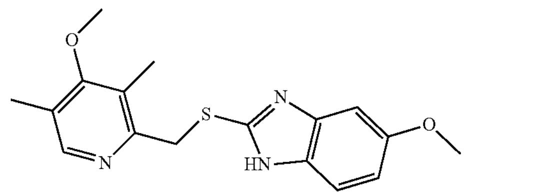

(IVa)

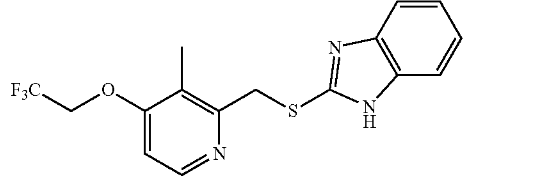

(Va)

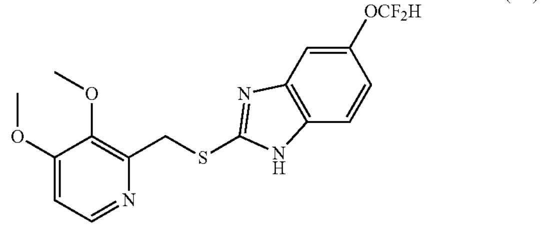

(VIa)

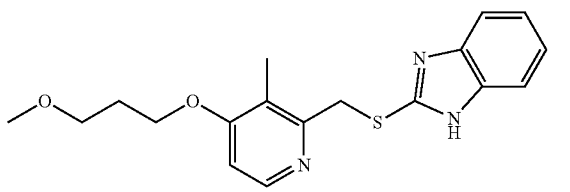

(VIIa)

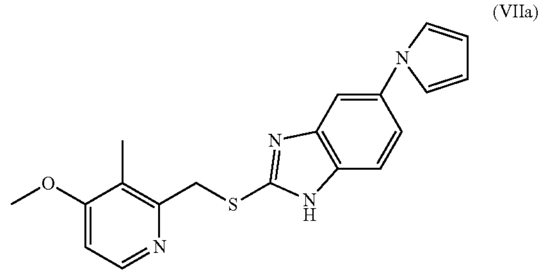

It should be noted that, the "Xaa number" of the present invention refers to the amino acid residue at position "number" of the amino acid sequence, e.g., "Xaa40" refers to the amino acid residue at position "40" of the amino acid sequence.

The "amino acid residue (a)+Xaa number" of the present invention means that the amino acid residue at position "number" of the amino acid sequence is "amino acid residue (a)", and can also be abbreviated as "amino acid residue (a)+number"; e.g., "K326" means that the amino acid residue at position "326" of the amino acid sequence is "K" (lysine).

The "amino acid residue (a)+Xaa number+amino acid residue (b)" of the present invention means that the amino acid residue at position "number" of the amino acid sequence, that is, "amino acid residue (a)", is replaced with "amino acid residue (b)", and can also be abbreviated as "amino acid residue (a)+number+amino acid residue (b)"; e.g., "K326C" means that the amino acid residue at position "326" of the amino acid sequence, "K" (lysine), is replaced with "C" (cysteine).

In the present invention, unless otherwise specified, the "number" in "Xaa number", "amino acid residue (a)+Xaa number", "amino acid residue (a)+number", "amino acid residue (a)+Xaa number+amino acid residue (b)", "amino acid residue (a)+number+amino acid residue (b)" means that the amino acid position in SEQ ID NO:2 is taken as a reference.

To address the defects of the prior art, the present invention resolves the crystalline structure of *Acinetobacter* thioether monooxygenase, establishes a high-throughput flat-plate transparent circle screening method, combines a rational design with a high-throughput screening, and obtains a monooxygenase having high catalytic activity. It is used as a catalyst in a small amount in the reaction, and significantly improves the catalytic activity of the enzyme and the space-time yield of the catalytic reaction. The reaction scale is not limited to the laboratory scale. It provides a new biocatalyst resource for the industrial synthesis of chiral sulfoxide drugs.

As compared with other existing methods of asymmetric oxidation, the use of the monooxygenase of the present invention to prepare chiral sulfoxide-based drugs has advantages including mild reaction conditions, environmental friendliness, high yield, high product optical purity, less peroxidation products, etc., and has a good industrial application prospect in the production of proton pump inhibitor drugs for treating gastric ulcers.

DETAILED DESCRIPTION OF THE EMBODIMENTS

Figure 1:
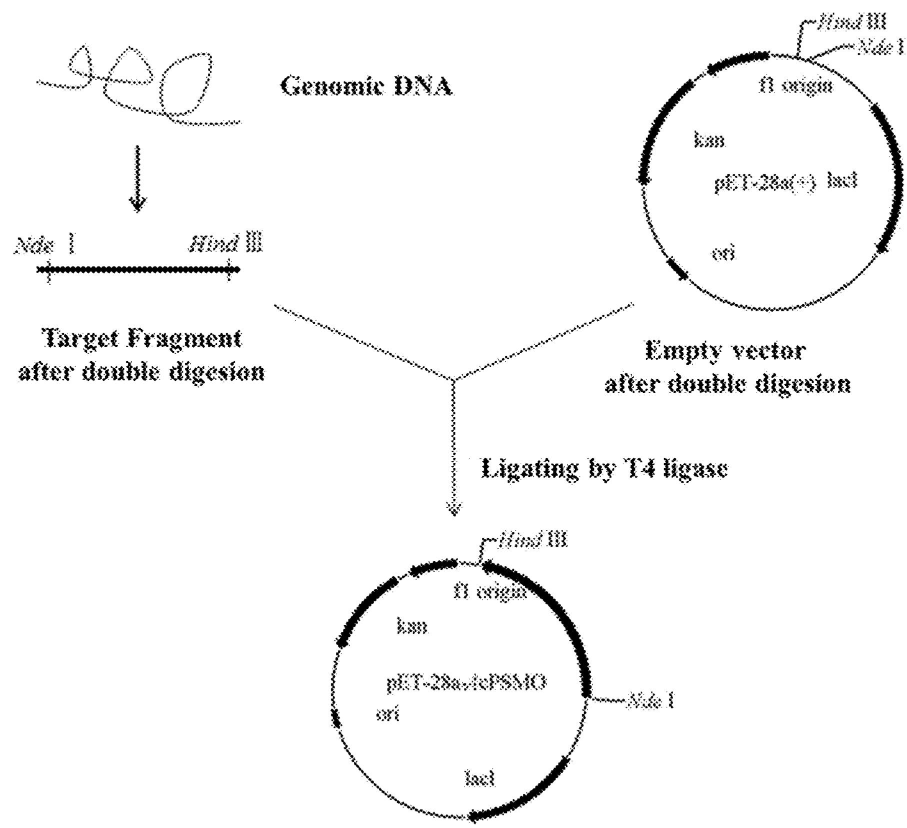
FIG. 1 is a construction view of the recombinant plasmid pET28a-AcPSMO.

By bioinformatics methods, the present invention analyzes and predicts the monooxygenase genes that may have oxidative activity on thioethers, and successively clones and expresses a variety of monooxygenase genes and demonstrates the functions thereof, wherein some demonstrating results are shown in Table 1. Of those, the recombinantly expressed thioether monooxygenase of the enzyme sequence WP_045432192.1 (NCBI Reference Sequence: WP_045432192.1; https://www.ncbi.nlm.nih.gov/) cloned from *Acinetobacter calcoaceticus* can effectively catalyze the oxidation of benzyl thioether (the compound of Formula IIa) to benzyl sulfoxide (the compound of Formula IIb). The thioether monooxygenase is named AcPSMO, and its amino acid sequence is shown in SEQ ID NO:2.

TABLE 1

Thioether Monooxygenase Catalyzes Benzyl Thioether to Benzyl Sulfoxide

| Entry | NCBI Accession Number | Microorganism | Conv. (%)[a] |
|---|---|---|---|
| AcPSMO | WP_045432192.1 | *Acinetobacter calcoaceticus* | 97 |
| TmPSMO | 5M10_A | *Thermocrispum municipale* | 88 |
| PsPSMO | WP_011486392.1 | *Polaromonas* sp. JS666 | 82 |
| AfPSMO | XP_002377626.1 | Aspergillus flavus NRRL3357 | 64 |
| RaPSMO | WP_029546891.1 | *Rhodococcus aetherivorans* | 62 |

[a]For experimental conditions, please refer to Example 9

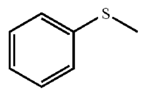

Formula IIa

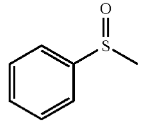

Formula IIb

*Acinetobacter calcoaceticus* as used in the present invention is deposited in the China General Microbiological Culture Collection Center (CGMCC, located at No. 3, Courtyard 1, West Beichen Road, Chaoyang District, Beijing City) with a date of deposit of Mar. 20, 2014 and an accession number of CGMCC No. 8936. When deposited, the strain was named *Acinetobacter* sp. in the certificate of deposit. *Acinetobacter* represents the name of genus, and *calcoaceticus* represents the name of species, wherein sp. represents an unknown name of species. After the date of deposit and by the filing date of the present patent application, the inventor further identified the name of species of *Acinetobacter* sp. in the certificate of deposition, that is, *Acinetobacter calcoaceticus.*

The naturally existing monooxygenase AcPSMO has a lower catalytic activity for catalyzing the oxygenation preparation of certain sulfoxide compounds, e.g., oxidizing omeprazole thioether (the compound of Formula IIIa) to the compound of Formula IIIb or the like. By resolving the crystalline structure of the monooxygenase AcPSMO, the present invention finds creatively that the amino acid residues at some positions are key for affecting the access of substrate into the catalytic center and affecting the catalytic activity, and provides through extensive studies a monooxygenase having an amino acid sequence obtained by replacements of any 2 or more amino acid residues at the specified positions of the amino acid sequence shown in SEQ ID NO:2; e.g., it can be obtained by replacements of amino acid residues at any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 of the specified positions.

The amino acid residues at the specified positions are selected from the group consisting of: at Xaa21; at Xaa40; at Xaa55; at Xaa70; at Xaa143; at Xaa145; at Xaa156; at Xaa185; at Xaa220; at Xaa244; at Xaa246; at Xaa248; at Xaa249; at Xaa277; at Xaa281; at Xaa326; at Xaa386; at Xaa388; at Xaa390; at Xaa405; at Xaa426; at Xaa430; at Xaa432; at Xaa433; at Xaa435; at Xaa438; at Xaa465; at Xaa468; at Xaa488; at Xaa489; at Xaa490; at Xaa497; at Xaa501; at Xaa505.

Further optionally, the replacements of amino acid residues at the specified positions include those selected from the group consisting of:

at Xaa21, S is replaced with G; at Xaa40, T is replaced with A; at Xaa55, L is replaced with Y, W, F or N; at Xaa70, E is replaced with G; at Xaa143, L is replaced with P or A; at Xaa145, A is replaced with S; at Xaa156, E is replaced with G; at Xaa185, G is replaced with A or S; at Xaa220, M is replaced with R; at Xaa244, L is replaced with V or I; at Xaa246, F is replaced with Y; at Xaa248, L is replaced with E, N, A or W; at Xaa249, N is replaced with S; at Xaa277, F is replaced with L, V, Y, I or D; at Xaa281, F is replaced with V or A; at Xaa326, K is replaced with C or F; at Xaa386, N is replaced with S; at Xaa388, I is replaced with F, C, K, G; at Xaa390, M is replaced with S, V, I; at Xaa405, K is replaced with M; at Xaa426, L is replaced with F or P; at Xaa430, G is replaced with T or S; at Xaa432, F is replaced with L or I; at Xaa433, T is replaced with C or A; at Xaa435, L is replaced with S; at Xaa438, S is replaced with I; at Xaa465, K is replaced with R; at Xaa468, V is replaced with A; at Xaa488, E is replaced with K; at Xaa489, S is replaced with C; at Xaa490, W is replaced with R; at Xaa497, P is replaced with S; at Xaa501, N is replaced with Y; At Xaa505, F is replaced with L.

By the above-described replacements, it can either promote the substrate to enter the activation center, increasing the catalytic activity; or can reduce the reaction by-products, increasing the purity of the product.

Figure 2:
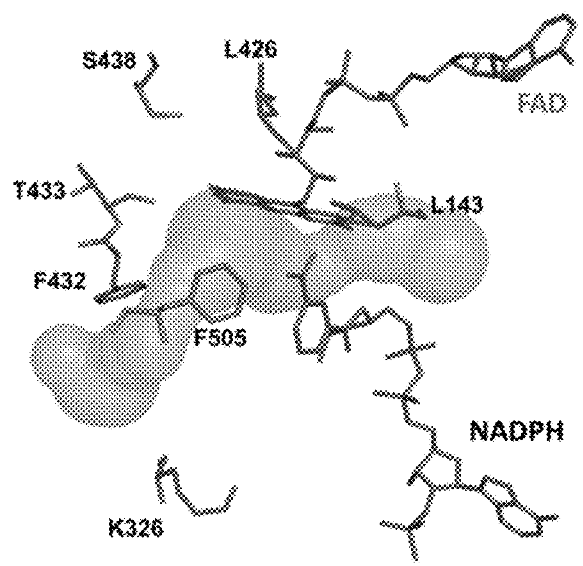
FIG. 2 is a view showing the substrate passage of the monooxygenase AcPSMO and key sites thereof.

The naturally existing monooxygenase AcPSMO can oxidize and convert benzyl thioether (the compound of Formula IIa) to benzyl sulfoxide (the compound of Formula IIb), but the activity for oxidizing omeprazole thioether (the compound of Formula IIIa) to the compound of Formula IIIb is very low. Referring to FIG. 2, the present invention resolves the crystalline structure of the monooxygenase AcPSMO, predicts the entrance and exit tunnels of the substrate, and finds that the entrance tunnel of the compound of Formula IIIa has a significant bottleneck portion, wherein the residues L143, K326, L426, F432, T433, 5438 and F505 are keys affecting the entrance of the substrate compound of Formula IIIa into the catalytic center.

Formula IIIa

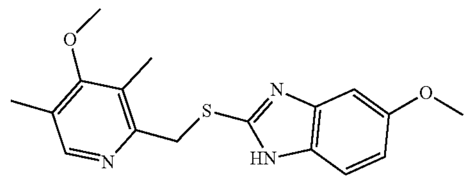

Formula IIIb

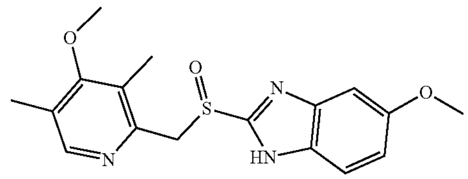

In some embodiments, the catalytic substrate specificity of the monooxygenase AcPSMO mutant modified against the above-described key sites has changed, so that the activity for converting the compound of Formula IIIa to the compound of Formula IIIb is increased by more than 5 folds. Exemplary amino acid sequences of the monooxygenase AcPSMO mutants are selected from the group consisting of SEQ ID NOS: 4, 6, 8, 10, 12, 14, 16, 18, 20, 22, 24, 26, of which the oxidative activity relative to the monooxygenase AcPSMO (SEQ ID NO: 2) is shown in Table 2. The(S)-configuration of the compound of Formula IIIb is just esomeprazole.

TABLE 2

Monooxygenase AcPSMO Mutant with Improved Properties

| SEQ ID NO: (nt/AA) | Difference of Residues | Activity | Configuration | ee Value |
|---|---|---|---|---|
| 1/2 | — | 1.0 | — | — |
| 3/4 | K326C/F432L | + | S | / |
| 5/6 | K326F/F432L | + | S | / |
| 7/8 | K326C/F432I | + | S | / |
| 9/10 | K326C/F432L/L435S/S438I | ++ | S | 57 |
| 11/12 | K326F/F432L/L435S/S438I | ++ | S | / |
| 13/14 | K326C/F432L/T433C/L435S/S438I | ++ | S | 84 |
| 15/16 | K326C/F432L/T433A/L435S/S438I | ++ | S | 83 |
| 17/18 | K326C/L426F/F432L/T433A/L435S/S438I | ++ | S | 69 |

TABLE 2-continued

| Monooxygenase AcPSMO Mutant with Improved Properties | | | | |
|---|---|---|---|---|
| SEQ ID NO: (nt/AA) | Difference of Residues | Activity | Configuration | ee Value |
| 19/20 | K326C/L426P/F432L/T433A/L435S/S438I | ++ | S | / |
| 21/22 | K326C/L426F/F432L/T433A/L435S/S438I/F505L | +++ | S | 93 |
| 23/24 | L143P/K326C/L426F/F432L/T433A/L435S/S438I/F505L | ++++ | S | 98 |
| 25/26 | L143A/K326C/L426F/F432L/T433A/L435S/S438I/F505L | ++++ | S | 98 |

"nt" in SEQ ID NO: (nt/AA) represents nucleotide, "AA" represents amino acid.
"Difference of residue" refers to the difference of amino acid residue relative to SEQ ID NO: 2.
"Activity" refers to the activity of oxidizing the compound of Formula IIIa to the compound of Formula IIIb, and is expressed as a relative value as compared with an enzyme represented by SEQ ID NO: 2.
+ represents > 5 folds,
++ represents > 50 folds,
+++ represents > 500 folds,
++++ represents > 5000 folds
"Configuration" represents the configuration of the product, that is, the compound of Formula IIIb.
"ee value" refers to the ee value of the product, that is, the compound of Formula IIIb.

Figure 3:
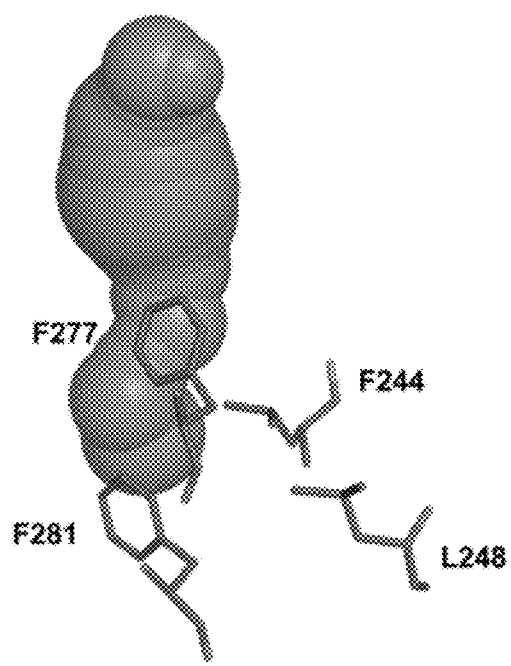
FIG. 3 is a view showing the key sites affecting the production of by-products in the structure of the monooxygenase AcPSMO.

During the enzymatic catalytic oxidation of the compound of Formula IIIa, the compound of Formula IIIb will be excessively oxidized to produce the by-product, the compound of Formula IIIc, and finally cause a substantial decrease of the purity and yield of the target product, the compound of Formula IIIb, which is not conducive to industrial production. As shown in FIG. 3, on the basis of the resolved crystalline structure of the monooxygenase AcPSMO, the present invention finds that the key sites affecting the selectivity of substrate and the production of the peroxidized by-products, the compound of the formula IIIc, are F277, L248, L244 and F281.

Formula IIIc

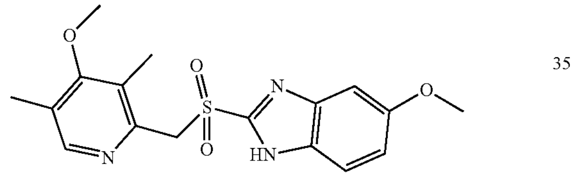

In some embodiments, the monooxygenase AcPSMO mutant obtained by modification of the above-described key sites reduces the production of the by-product, the compound of Formula IIIc, and increases the ratio of the activity of the compound of Formula IIIa to the oxidative activity of the compound of Formula IIIb by 1.5 folds or more relative to SEQ ID NO:22. Exemplary monooxygenase AcPSMO mutants have amino acid sequences selected from the group consisting of SEQ ID NOS:28, 30, 32, 34, 36, 38, 40, 42, 44, 46, 48, 50, 52, 54, 56; of which the increase of substrate selectivity relative to SEQ ID NO:22 is shown in Table 3; wherein the compound of Formula IIIb in Table 3 is the (9-configuration of the compound of Formula IIIb.

TABLE 3

| Monooxygenase AcPSMO Mutant with Decreased Production of By-Products | | |
|---|---|---|
| SEQ ID NO: (nt/AA) | Difference of Residues | Substrate Selectivity |
| 21/22 | K326C/L426F/F432L/T433A/L435S/S438I/F505L | 1.0 |
| 27/28 | L244V/K326C/L426F/F432L/T433A/L435S/S438I/F505L | + |
| 29/30 | L244I/K326C/L426F/F432L/T433A/L435S/S438I/F505L | + |
| 31/32 | L143P/L248E/K326C/L426F/F432L/T433A/L435S/S438I/F505L | + |
| 33/34 | L248N/K326C/L426F/F432L/T433A/L435S/S438I/F505L | + |
| 35/36 | L248A/K326C/L426F/F432L/T433A/L435S/S438I/F505L | + |
| 37/38 | L248W/K326C/L426F/F432L/T433A/L435S/S438I/F505L | + |
| 39/40 | L143P/F277L/K326C/L426F/F432L/T433A/L435S/S438I/F505L | +++ |
| 41/42 | L143P/F277V/K326C/L426F/F432L/T433A/L435S/S438I/F505L | +++ |
| 43/44 | L143P/F277Y/K326C/L426F/F432L/T433A/L435S/S438I/F505L | ++ |

TABLE 3-continued

| Monooxygenase AcPSMO Mutant with Decreased Production of By-Products | | |
|---|---|---|
| SEQ ID NO: (nt/AA) | Difference of Residues | Substrate Selectivity |
| 45/46 | F277I/K326C/L426F/F432L/T433A/L435S/S438I/F505L | +++ |
| 47/48 | F277D/K326C/L426F/F432L/T433A/L435S/S438I/F505L | +++ |
| 49/50 | F281V/K326C/L426F/F432L/T433A/L435S/S438I/F505L | + |
| 51/52 | F281A/K326C/L426F/F432L/T433A/L435S/S438I/F505L | + |
| 53/54 | L143P/F277L/F281V/K326C/L426F/F432L/T433A/L435S/S438I/F505L | +++ |
| 55/56 | L143P/F277V/F281A/K326C/L426F/F432L/T433A/L435S/S438I/F505L | +++ |

"nt" in SEQ ID NO: (nt/AA) represents nucleotide, "AA" represents amino acid

"Difference of Residues" refers to the difference of amino acid residues relative to SEQ ID NO: 2

"Substrate Selectivity" refers to the ratio of the oxidative activity of the compound of Formula IIIa to the oxidative activity of the compound of Formula IIIb, expressed as the relative value relative to the enzyme as represented by SEQ ID NO: 22

+ represents > 1.5,

++ represents > 5,

+++ represents > 10

Based on the solubility difference between the substrate compound of Formula IIIa and the product compound of Formula IIIb, the present invention provides a flat transparent circle high-throughput screening method. A solution of the substrate compound of Formula IIIa is spread on a plate and shows a milky white opaque state. When the colony grows for 12 hours, the expressed polypeptide will convert a part of the compound of Formula IIIa into the product compound of Formula IIIb. The product compound of Formula IIIb gradually produces a transparent circle due to its higher solubility than the compound IIIa. A mutant library is constructed by directed evolution, and enzymes with higher activity are screened based on the transparent circle method.

In some embodiments, based on the above-described high throughput transparent circle screening method, the obtained monooxygenase AcPSMO mutant can convert the compound of Formula IIIa into the compound of Formula IIIb with an activity of 1.5 times greater than that of SEQ ID NO: 40. The monooxygenase AcPSMO mutant has an amino acid sequence selected from the group consisting of SEQ ID NOS:58, 60, 62, 64, 66, 68, 70, 72, 74, 76, 78, 80, 82, 90, 92, 94, 96, 98.

TABLE 4

| Monooxygenase AcPSMO Mutant with Improved Activities Obtained Based on High Throughput Screening | | |
|---|---|---|
| SEQ ID NO: (nt/AA) | Difference of Residues | Activity |
| 39/40 | L143P/F277L/K326C/L426F/F432L/T433A/L435S/S438I/F505L | 1.0 |
| 57/58 | L143P/M220R/F277L/K326C/L426F/F432L/T433A/L435S/S438I/K465R/F505L | + |
| 59/60 | L143P/G185A/F277L/K326C/L426F/F432L/T433A/L435S/S438I/F505L | + |
| 61/62 | L143P/F246Y/F277L/K326C/L426F/F432L/T433A/L435S/S438I/F505L | ++ |
| 63/64 | L143P/F277L/K326C/K405M/L426F/F432L/T433A/L435S/S438I/N501Y/F505L | + |
| 65/66 | L143P/E156G/F277L/K326C/L426F/F432L/T433A/L435S/S438I/F505L | + |
| 67/68 | L143P/N249S/F277L/K326C/L426F/F432L/T433A/L435S/S438I/F505L | + |
| 69/70 | T40A/L143P/F277L/K326C/L426F/F432L/T433A/L435S/S438I/F505L | + |
| 71/72 | L143P/F277L/K326C/L426F/F432L/T433A/L435S/S438I/S489C/W490R/F505L | ++ |
| 73/74 | L143P/F246Y/F277L/K326C/L426F/F432L/T433A/L435S/S438I/S489C/W490R/F505L | +++ |
| 75/76 | L143P/F246Y/F277L/K326C/L426F/F432L/T433A/L435S/S438I/S489C/W490R/N501Y/F505L | +++ |
| 77/78 | L143P/F246Y/F277L/K326C/N386S/L426F/F432L/T433A/L435S/S438I/S489C/W490R/N501Y/F505L | +++ |
| 79/80 | L143P/F246Y/F277L/K326C/N386S/I388F/L426F/F432L/T433A/L435S/S438I/S489C/W490R/N501Y/F505L | +++ |
| 81/82 | L143P/F246Y/F277L/K326C/N386S/I388K/M390I/L426F/F432L/T433A/L435S/S438I/S489C/W490R/N501Y/F505L | +++ |
| 89/90 | L143P/F246Y/F277L/K326C/N386S/I388K/M390I/L426F/F432L/T433A/L435S/S438I/E488K/S489C/W490R/F505L | +++ |
| 91/92 | S21G/L55Y/E70G/L143P/F246Y/F277L/K326C/N386S/I388K/M390I/L426F/F432L/T433A/L435S/S438I/S489C/W490R/N501Y/F505L | +++ |
| 93/94 | S21G/L55Y/E70G/L143P/G185S/F246Y/F277L/K326C/N386S/I388K/M390I/L426F/F432L/T433A/L435S/S438I/S489C/W490R/P497S/N501Y/F505L | +++ |

TABLE 4-continued

Monooxygenase AcPSMO Mutant with Improved Activities Obtained Based on High Throughput Screening

| SEQ ID NO: (nt/AA) | Difference of Residues | Activity |
|---|---|---|
| 95/96 | S21G/L55Y/E70G/L143P/A145S/G185S/F246Y/F277L/K326C/N386S/I388K/M390I/L426F/F432L/T433A/L435S/S438I/S489C/W490R/P497S/N501Y/F505L | +++ |
| 96/98 | S21G/L55Y/E70G/L143P/A145S/G185S/F246Y/F277L/K326C/N386S/I388K/M390I/L426F/G430T/F432L/T433A/L435S/S438I/S489C/W490R/P497S/N501Y/F505L | +++ |

"nt" in SEQ ID NO: (nt/AA) represents nucleotide, "AA" represents amino acid

"Difference of Residues" refers to the difference of amino acid residues relative to SEQ ID NO: 2

"activity" refers to the activity for oxidizing the compound of Formula IIIa to the compound of Formula IIIb, expressed by a relative value relative to the enzyme represented by SEQ ID NO: 40

+ represents > 1.5,

++ represents > 5,

+++ represents > 10

Optionally, the amino acid residue(s) at positions other than the specified positions can be further treated by any one or more mutations of replacements, deletions, and insertions. The above-described mutations include:

(a) replacements of amino acid residue(s) at any 1, 2, 3, 4, or 5 positions other than the specified positions;

(b) deletions of amino acid residue(s) at any 1, 2, 3, 4, or 5 positions other than the specified positions; and (c) insertions of amino acid residue(s) at any 1, 2, 3, 4, or 5 positions other than the specified positions.

It should be noted that, the replacements (deletions, insertions) of amino acid residue(s) at 1, 2, 3, 4, or 5 positions refers to replacement (deletion, insertion) of 1, 2, 3, 4, or 5 amino acid residue(s).

The present invention provides a nucleic acid sequence encoding the monooxygenase AcPSMO mutant, and the nucleic acid molecule includes, but is not limited to: a naturally existing nucleic acid molecule encoding the monooxygenase AcPSMO extracted from an organism, a nucleic acid molecule encoding the monooxygenase AcPSMO mutant obtained by engineering of an existing nucleic acid fragment via a gene cloning technology, or a nucleic acid molecule encoding the monooxygenase AcPSMO mutant obtained by an artificial synthetic method. The terms "nucleic acid" and "nucleic acid molecule" are interchangeably used herein, and refer to a single- or double-strand deoxyribonucleotide or ribonucleotide and their polymers.

The present invention provides a recombinant expression vector including a nucleic acid sequence encoding the above-described monooxygenase AcPSMO mutant. Due to the degeneracy of codons, the nucleic acid sequence encoding the same monooxygenase AcPSMO mutant may not be unique. The recombinant expression vector can be constructed by linking a nucleic acid sequence encoding the above-described monooxygenase AcPSMO mutant to a variety of suitable vectors by conventional technology in the art. Of those, the vectors can be various conventional vectors in the art, such as, commercially available plasmids, cosmids, phages, or viral vectors, etc. Further, the vector is preferably a plasmid. The recombinant expression vector prepared by conventional technical means in the art can be a recombinant expression plasmid. More preferably, the plasmid is plasmid pET28a.

The present invention provides a recombinant expression transformant including the above-described recombinant expression vector. The recombinant expression transformant can be prepared by transforming the recombinant expression vector of the present invention into a host cell. Of those, the host cell can be various conventional host cells in the art, provided that the recombinant expression vector can be stably auto-replicated, and the monooxygenase segregation gene carried thereby can be effectively expressed. The present invention prefers *E. Coli*, preferably *E. coli* BL21 (DE3).

The PCR product containing the monooxygenase AcPSMO gene (shown in SEQ ID NO: 1) obtained by PCR amplification is double digested with restriction enzymes Nde I and Hind III to form complementary cohesive ends. Meanwhile, the expression vector pET28a is double digested with restriction enzymes Nde I and Hind III. The digested gene fragments are ligated to an expression vector through T4 DNA ligase to generate the recombinant expression plasmid pET28a-AcPSMO containing the monooxygenase gene of the present invention, as shown in FIG. 1. The recombinant expression plasmid pET28a-AcPSMO is transformed into *E. coli* BL21 (DE3) to obtain a genetically engineered strain expressing the monooxygenase AcPSMO, namely, *E. coli* BL21 (DE3)/pET28a-AcPSMO. Through similar methods, it is easy to obtain genetically engineered strains expressing various mutants of the monooxygenase AcPSMO of the present invention. Alternatively, the pET28a-AcPSMO or its mutant is used as a template to produce a recombinant plasmid expressing the above-described monooxygenase AcPSMO mutant by site-directed mutagenesis or random mutation method, and then produce genetically engineered strains expressing various mutants of the monooxygenase AcPSMO of the present invention.

The present invention discloses a method of preparing the above-described monooxygenase, including culturing the above-described recombinant expression transformant, and then isolating the monooxygenase therefrom.

The method and conditions of culturing the recombinant expression transformant of the present invention are not particularly limited, and can be suitably selected according to different factors such as the host cell type and culture method based on common knowledge in the field, as long as the transformant can grow and efficiently produce the monooxygenase AcPSMO mutant of the present invention. When the recombinant expression transformant of the present invention is *E. coli*, an LB medium is preferable to culture the recombinant expression transformant and induce the enzyme production. The medium contains 10 g/L of peptone, 5 g/L of yeast extract, 10 g/L of NaCl, and is at a pH of 7.0. The culture of the recombinant expression transformant and the production of the monooxygenase AcPSMO mutant are preferably performed as follows: the recombinant *E. coli* (preferably, *E. coli* BL21 (DE3)) involved in the present invention is inoculated into an LB medium containing kanamycin for culture. When the optical density $OD_{600}$ of the culture medium reaches 0.5-0.7 (preferably, 0.6), the recombinant monooxygenase of the present invention can be effectively expressed under the induction of isopropyl-β-D-thiogalactopyranoside (IPTG) with a final concentration of 0.1-1.0 mmol/L (preferably 0.2 mmol/L) and 50-100 mg/L of vitamin B.

The monooxygenase AcPSMO mutant can be isolated from the recombinant expression transformant by conventional technical means in the art. An exemplary method is as follows: The fermentation liquor of recombinant *E. coli* (including but not limited to shake flask culture, fermentor culture) is centrifuged and collected for the recombinant *E. coli* cells. The cells are resuspended in a potassium phosphate buffer (KPB buffer, e.g., 100 mM, pH=9.0), and then subject to ultrasonication or high-pressure homogenization. The fragmentized liquors are centrifuged to collect the supernatant enzyme solution which can be further freeze-dried to produce a freeze-dried enzyme powder. The exemplary ultrasonication is performed under the conditions of a power of 400 W, an operation for 4 s, an interval of 6 s, and 99 cycles. The high-pressure homogenization is performed under the conditions of 700-800 bars, 2 cycles.

The present invention further provides use of the above-described monooxygenase AcPSMO mutant for asymmetric catalytic oxidation of a prochiral thioether compound. Preferably, the monooxygenase asymmetrically catalyzes the oxidation of a prochiral thioether compound to a sulfoxide compound. Preferably, the prochiral thioether compound is selected from the group consisting of the compound of Formula IIIa or compounds presented by any one of the following formulae:

(IVa)

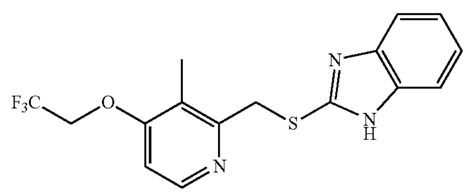

(Va)

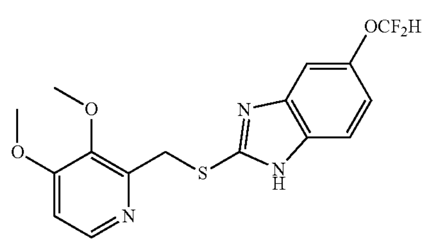

(VIa)

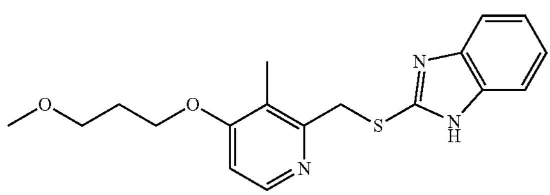

-continued (VIIa)

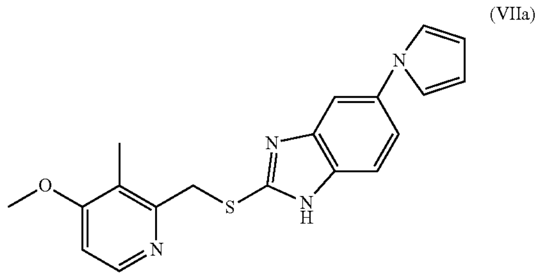

Of those, the present invention calls the compound of Formulae IIIa, IVa, Va, VIa, VIIa as omeprazole thioether, lansoprazole thioether, pantoprazole thioether, rabeprazole thioether, Ilaprazolethioether, respectively. Of course, they can also be named in different ways in other documents.

By use of the monooxygenase AcPSMO mutant of the present invention for asymmetrically catalyzing the oxidation of the prochiral thioether compound to the sulfoxide compound, the specific reaction conditions as involved, such as, substrate concentrations, pH, composition of buffer, amount of enzymes, and the like, can be selected in line with conventional conditions of such reactions in the art. Further, the asymmetrical catalytic oxidation can be performed under shaking or stirring.

In some embodiments, the harvested supernate enzyme solution or lyophilized enzyme powder is suspended in a potassium phosphate buffering solution (pH 8.5-10), and a solution of the substrate of Formula IIIA is added and reacted at 20-35° C. for 6-48 hr.

In some embodiments, a co-solvent is used to solubilize the thioether substrate, e.g., methanol, ethanol, acetonitrile, isopropanol, acetone, t-butyl alcohol, dimethyl formamide (DMF) and dimethyl sulfoxide (DMSO) at a ratio of 2%-10% (v/v); and hydroxypropyl-β-cyclodextrin, PEG, Triton, Span or Tween additives are added at a ratio of 0.1%-1.5% (w/w) to facilitate the dispersion of substrates.

In some embodiments, a cofactor regeneration system is used to regenerate $NADP^+$ to NADPH, e.g., formate dehydrogenase for oxidizing formate to generate $CO_2$ or alcohol dehydrogenase for oxidizing isopropanol to generate acetone is used to achieve the regeneration of reducing cofactors.

The monooxygenase AcPSMO of the present invention or its mutant can be measured for their activity on the compound of Formula IIIa or the compound of Formula IIIb by the following method: 0.5 mL of reaction system (100 mmol/L of KPB buffer solution, pH 9.0) containing 1 mmol/L of the compound of Formula IIIa or the compound of Formula IIIb and 0.2 mmol/L of NADPH is pre-heated to 30° C., and then an appropriate amount of thioether monooxygenase is added, the mixture is maintained at 30° C. and reacted with shaking, and then detected for the generation of the product by liquid chromatography.

The conversion of the monooxygenase AcPSMO of the present invention or its mutant for oxidizing the compound of Formula IIIa can be measured by the following method: 0.5 mL of reaction system (100 mmol/L of KPB buffer solution, pH 9.0, 2% (v/v) DMSO) containing 2 mmol/L of the compound of Formula IIIa and 2 mmol/L of NADPH is pre-heated to 30° C., and then an appropriate amount of thioether monooxygenase is added, the mixture is maintained at 30° C. and reacted with shaking, and then detected for the generation of the product by liquid chromatography.

In the present invention, the monooxygenase AcPSMO is subject to multiple rounds of molecular modification by protein engineering, and the constructed monooxygenase AcPSMO mutant can convert the compound of Formula IIIa into the compound of Formula IIIb with higher activity, thermal stability, and yield of product.

The following examples are a further description of the present invention, rather than a limitation. Unless otherwise specified, the materials and reagents as used are common commercially available products, and the method and operations as used are conventional operations in the art.

Example 1 Gene Clone of Monooxygenase AcPSMO

According to the open reading frames (ORF) of the monooxygenase AcPSMO, the upstream and the downstream primers are designed as follows:

```
Upstream primer SEQ ID NO: 83:
GGGAATTCCATGATGACCCAGAAGATGGACTT

Downstream primer SEQ ID NO: 84:
CCCAAGCTTTTAGCTTTCGATCAGGTTGG
```

Of those, the underlined portion of the upstream primer is Nde I enzyme digestion sites, and the underlined portion of the downstream primer is Hind III enzyme digestion sites.

With the genomic DNA of *Acinetobacter calcoaceticus* WP_045432192.1 as a template, PCR amplification was performed. The PCR system includes: 2×Taq PCR MasterMix 25 μL, upstream primer and downstream primer (10 ng/μL) each 2.5 μL, genomic DNA (100 ng/μL) 1 μL, and $ddH_2O$ 19 μL. The PCR amplification procedure includes: pre-denaturation at 95° C. for 5 minutes, followed by 32 cycles of denaturation at 94° C. for 30 seconds, annealing at 50° C. for 40 seconds, stretching at 72° C. for 1.5 minutes; and finally stretching at 72° C. for another 10 minutes. After the PCR amplification products were purified by gel electrophoresis, a DNA recovery kit was used to recover the target fragments. By DNA sequencing, the open reading frame encoded in the sequence is 1629 bp in length, and has a base sequence shown in SEQ ID NO: 1.

Example 2 Preparation of Monooxygenase AcPSMO Recombinant Expression Plasmid and Recombinant Expression Transformant As shown in FIG. 1, both the target fragments of the monooxygenase AcPSMO obtained by the PCR amplification in Example 1 and pET28a-empty plasmid were double digested with restrictive enzymes Nde I and Hind III overnight, purified by agarose gel electrophoresis, and recovered by a DNA recovery kit. The digested target fragments and empty plasmid vector were ligated in the presence of T4 DNA ligase at 4° C. for 12 hr to give the recombinant plasmid pET28a-AcPSMO.

The obtained recombinant plasmid was transformed into *E. coli* BL21 (DE3), coated onto an LB medium plate containing 50 μg/mL of kanamycin, and cultured at 37° C. for 12-16 hr. The grown colonies were subject to colony PCR verification, and picked colonies for PCR amplification to positive clones of the target bands with a length of about 1629 bp. By sequencing verification, the recombinant expression transformant *E. coli* BL21 (DE3)/pET 28a-AcPSMO was obtained.

Example 3 Induced Expression and Activity Measurement of Monooxygenase AcPSMO

The recombinant expression transformant *E. coli* BL21 (DE3)/pET28a-AcPSMO obtained in Example 2 was inoculated into an LB medium containing 50 μg/mL of kanamycin, incubated in a shaker at 37° C. for 12 hr, and then inoculated into a 500 mL conical flask charged with 100 mL of LB medium in an inoculating amount of 1% (v/v). The mixture was cultured in a shaker at 180 rpm at 37° C. When the $OD_{600}$ of the culturing medium reached 0.6, IPTG was added to a final concentration of 0.1 mmol/L, and vitamin B complex was added to a final concentration of 70 mg/L for induction. After induction at 16° C. for 24 h, the culturing medium was centrifuged at 15000 rpm for 5 min, collected for cells, and washed by normal saline to give resting cells. The obtained cells were resuspended in 10 mL of KPB buffer solution (100 mM, pH 9.0), and subject to ultrasonication in ice-water bath under conditions of a power of 400 W, an operation for 4 s, an interval for 6 s, and 99 cycles. The mixture was centrifuged at 4° C. at 15000 rpm for 40 min. The supernatant enzyme solution was collected, and lyophilized to produce lyophilized enzyme powder. The activity was detected in accordance with the method of Example 8 (Measurement of Oxidation Activity of Compound of Formula IIIa) as 58 U/g lyophilized enzyme powder.

Figure 4:
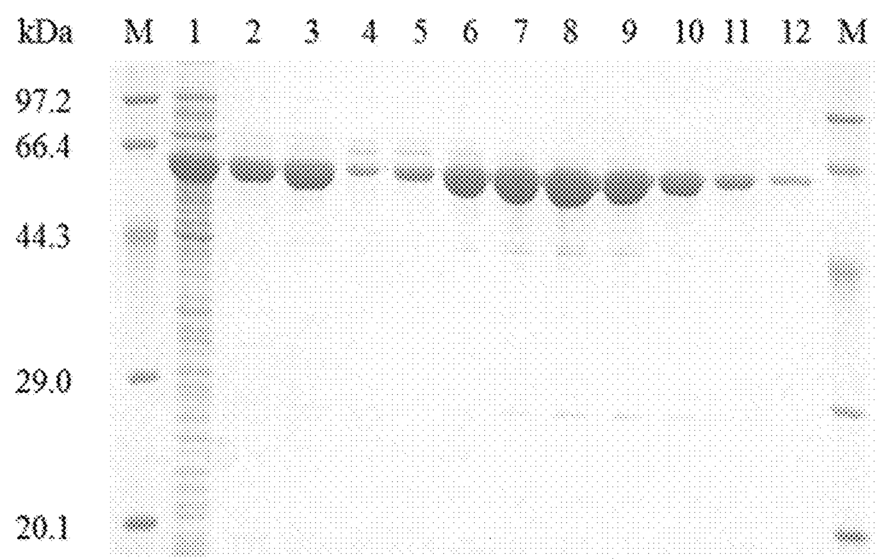
FIG. 4 is an SDS-PAGE diagram of crystallization grade purification, where lane 1 is the crushing solution, lane 2 is the Ni eluent, lane 3 is the sample before loading of the molecular sieve, and lanes 4-12 are the samples after isolation of the molecular sieve.

Example 4 Purification, Crystallization and Structural Resolution of Monooxygenase AcPSMO Purification of Crystalline-Grade Protein The buffer solutions used in the purification process of Ni affinity self-packing column are: solution A: 50 mM of KPB pH8.0, 500 mM of NaCl, 10 mM of imidazole, 2 mM of β-mercapto ethanol; solution B: 50 mM of KPB pH8.0, 500 mM of NaCl, 300 mM of imidazole, 2 mM of 3-mercaptoethanol; solution C: 50 mM of KPB pH9.0, 150 mM of NaCl, 1 mM of DTT. The purification method is as follows:

the cells were re-suspended in solution A and then ultrasonicated. The crushed liquid was centrifuged at 4° C. at 12000 rpm in a low-temperature high-speed centrifuge for 45 min. The centrifuged supernatant was temporarily stored in a 4° C. refrigerator or cold storage;

Ni column was pre-equilibrated with 5-10 times column volume of solution A;

injecting the supernatant stored in step a);

d) after completion of injection, washing with 5-10 times column volume of mixed solution of A and B (10% solution B, v/v) to remove impurity proteins;

e) eluting and collecting the target protein with 1 column volume of solution B;

f) concentrating the collected target protein with a 30 kDa ultrafiltration tube;

g) rinsing the molecular gel column with 1 column volume of pure water, and equilibrating the column with 1 column volume of solution C at a flowrate of 0.5 mL/min (which can be adjusted in accordance with the column pressure);

h) injecting the protein obtained in step f) into the gel column with an injection volume of 2 mL and a protein concentration controlled within 10 mg/mL;

i) elution: eluting the protein with solution C, collecting the target protein in accordance with peak time at 280 nm, and demonstrating the concentration of the collected protein by SDS-PAGE, as shown in FIG. 4; and j) concentrating the combined samples with required purity by ultrafiltration with a 30 kDa ultrafiltration tube to a suitable concentration, sub-packing and quick-freezing the concentrates with liquid nitrogen, and storing in a −80° C. ultra-low temperature refrigerator.

(2) Primary Screening and Condition Optimization of Crystals

The high-purity enzyme solution obtained in step (1) was thawed on ice and centrifuged at 4° C. to remove precipitate. The crystallization concentrations of protein were first screened with a Pre Crystallization Test (PCT) kit for the screening of crystal growth conditions, and 14 mg/mL was finally selected as the crystallization concentration of protein based on the conditions of protein precipitation. The target protein was diluted with solution C to this concentration for primary screening of crystals.

First, the crystallization reagent in the crystallization kit was added into a 96-well sessile drop plate with 75 μL in each well. 1 μL of the diluted enzyme solution and 1 μL of the corresponding bath solution were added to each sessile drop hole and mixed well, and be careful to avoid generation of any bubbles. After addition, the crystallization sieve for primary screening was sealed with a sealing film, and placed in an 18° C. constant-temperature crystallization incubator. After a period of time (three days) of crystal growth, it was regularly observed with an SX10 microscope for the crystal growth. Conditions suitable for crystal growth were recorded once they appeared in the primary screening plate, and the bath solutions components corresponding thereto were found. The conditions were subject to optimization in a 24-well crystal secondary screening plate, mainly for the optimization of the pH of the crystal growth, the concentration of the precipitation agent, the salt concentration, etc. One primary screening condition was optimized in each secondary screening plate. A single crystal that grew well was taken by a cryoloop of an appropriate size from the crystal secondary screening plate, and quickly placed in a cryoprotectant. After a certain period of equilibrium in the cryoprotectant, the crystal was quickly placed in liquid nitrogen for cryopreservation. Here, the cryoprotectant was optimized against different concentrations of glycerin, PEG and heavy oil, and finally 15% glycerol was selected as the cryoprotectant.

Data Acquisition and Processing of X-Ray Diffraction of Crystals

The crystals cryopreserved in liquid nitrogen were placed on the goniometer of the BL17U or BL19U X-ray diffractometer of the Shanghai Synchrotron Radiation Facility (Shanghai Synchrotron Radiation Facility) by using cryotong or other crystal transfer tools, and adjusted for their positions, followed by collection of the X-ray diffraction data. The collected diffraction data is a pattern, which is subject to data pre-processing by HKL2000. The pre-processing includes three steps of Index, Integrate and Scale. After being processed in the three steps, sca and log files will be generated, and that can be used for subsequent processing of crystal data.

Three softwares are mainly used in the subsequent processing: CCP4, Phenix and Coot. The specific processing scheme is as follows:

1) The sca file generated by the pre-processing is opened in CCP4 with the scalepack2mtz program, and converted to an mtz file. The number of protein molecules in each asymmetric unit is calculated with the Mattews coef program, and then homogeneous molecule replacement is performed by the Phaser MR program. Here, RmCHMO (PDB ID: 3UCL) is used as the template for molecule replacement. Finally, a pdb file is generated, that is also the preliminary three-dimensional structure file of the target protein.

2) The preliminary structure file is automatically optimized in the Phenix software.

3) In the Coot software, the structure is refined by the electron cloud density and the backbone of the amino acid residues in the primary sequence, so that the parameters such as R-free, R-work and Ramachandran map meet the standards. Finally, the intact crystal structure of the monooxygenase AcPSMO is obtained.

Example 5 Directed Mutation of Monooxygenase AcPSMO

Taking pET28a AcPSMO (Example 2) as a template and SEQ ID NO:85 and SEQ ID NO:86 as the upstream and the downstream primers, a high-fidelity PCR was performed by Primer Star polymerase. The reaction system is as follows: plasmid template (100 ng/μL), the upstream and the downstream primers (10 ng/μL) each 0.5 μL, DMSO 0.3 μL, $ddH_2O$ 8 μL, and 2× Prime Star 10 μL. PCR reaction procedure: pre-denaturation at 95° C. for 3 min, denaturation at 98° C. for 30 seconds, annealing at 55° C. for 15 seconds, stretching at 72° C. for 7.5 min; and finally stretching at 72° C. for additional 5 min. The PCR product was digested with Dpn I for 3-5 h, and the digested product was transformed into *E. coli* BL21 (DE3) competent cells, which were coated onto a plate containing kanamycin, and placed and cultured in a 37° C. incubator for about 12-16 h. The obtained monoclonal colony was sequenced, and extracted with a kit for its plasmid. The plasmid was used as a template, and SEQ ID NO:87 and SEQ ID NO:88 were used as the upstream and the downstream primers to repeat the aforesaid PCR. After the steps of digestion and transformation, the obtained monoclonal colony was sequenced. The base sequence thereof is shown in SEQ ID NO:3, and the amino acid sequence of the expressed monooxygenase AcPSMO mutant is shown in SEQ ID NO:4.

```
Upstream primer SEQ ID NO: 85:
ACCGACCTGTACGCGTGCCGTCCGCTGTGCGAT

Downstream primer SEQ ID NO: 86:
ATCGCACAGCGGACGGCACGCGTACAGGTCGGT

Upstream primer SEQ ID NO: 87:
GGCCCGAACGGTCCGCTGACCAACCTGCCGCCG

Upstream primer SEQ ID NO: 88:
CGGCGGCAGGTTGGTCAGCGGACCGTTCGGGCC
```

By using a method similar to that of obtaining the monooxygenase AcPSMO mutant shown in SEQ ID NO:4 and through suitable upstream and downstream primers, the following monooxygenase AcPSMO mutants can be obtained:

amino acid sequence shown in SEQ ID NO:6 (the corresponding base sequence is shown in SEQ ID NO:5);

amino acid sequence shown in SEQ ID NO:8 (the corresponding base sequence is shown in SEQ ID NO:7);

amino acid sequence shown in SEQ ID NO:10 (the corresponding base sequence is shown in SEQ ID NO:9);

amino acid sequence shown in SEQ ID NO:12 (the corresponding base sequence is shown in SEQ ID NO:11);

amino acid sequence shown in SEQ ID NO:14 (the corresponding base sequence is shown in SEQ ID NO:13);

amino acid sequence shown in SEQ ID NO:16 (the corresponding base sequence is shown in SEQ ID NO:15);

amino acid sequence shown in SEQ ID NO:18 (the corresponding base sequence is shown in SEQ ID NO:17);

amino acid sequence shown in SEQ ID NO:20 (the corresponding base sequence is shown in SEQ ID NO:19);

amino acid sequence shown in SEQ ID NO:22 (the corresponding base sequence is shown in SEQ ID NO:21);

amino acid sequence shown in SEQ ID NO:24 (the corresponding base sequence is shown in SEQ ID NO:23);

amino acid sequence shown in SEQ ID NO:26 (the corresponding base sequence is shown in SEQ ID NO:25);

amino acid sequence shown in SEQ ID NO:28 (the corresponding base sequence is shown in SEQ ID NO:27);

amino acid sequence shown in SEQ ID NO:30 (the corresponding base sequence is shown in SEQ ID NO:29);

amino acid sequence shown in SEQ ID NO:32 (the corresponding base sequence is shown in SEQ ID NO:31);

amino acid sequence shown in SEQ ID NO:34 (the corresponding base sequence is shown in SEQ ID NO:33);

amino acid sequence shown in SEQ ID NO:36 (the corresponding base sequence is shown in SEQ ID NO:35);

amino acid sequence shown in SEQ ID NO:38 (the corresponding base sequence is shown in SEQ ID NO:37);

amino acid sequence shown in SEQ ID NO:40 (the corresponding base sequence is shown in SEQ ID NO:39);

amino acid sequence shown in SEQ ID NO:42 (the corresponding base sequence is shown in SEQ ID NO:41);

amino acid sequence shown in SEQ ID NO:44 (the corresponding base sequence is shown in SEQ ID NO:43);

amino acid sequence shown in SEQ ID NO:46 (the corresponding base sequence is shown in SEQ ID NO:45);

amino acid sequence shown in SEQ ID NO:48 (the corresponding base sequence is shown in SEQ ID NO:47);

amino acid sequence shown in SEQ ID NO:50 (the corresponding base sequence is shown in SEQ ID NO:49);

amino acid sequence shown in SEQ ID NO:52 (the corresponding base sequence is shown in SEQ ID NO:51);

amino acid sequence shown in SEQ ID NO:54 (the corresponding base sequence is shown in SEQ ID NO:53); and amino acid sequence shown in SEQ ID NO:56 (the corresponding base sequence is shown in SEQ ID NO:55).

Figure 5A:
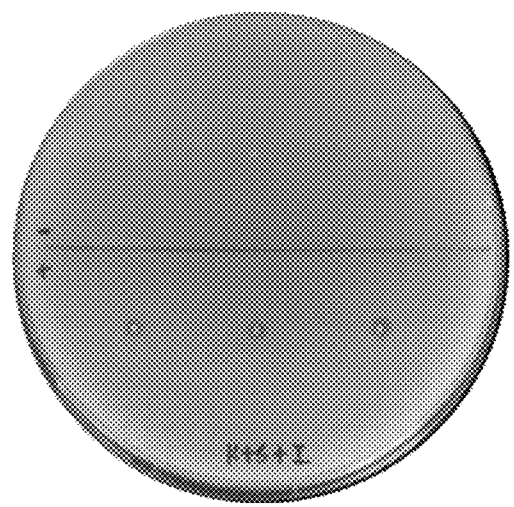
FIG. 5A is a construction view of the flat transparent circle screening method, in which "+" and "−" represent the AcPSMO mutants and AcPSMO (SEQ ID NO: 2), respectively.
Figure 5B:
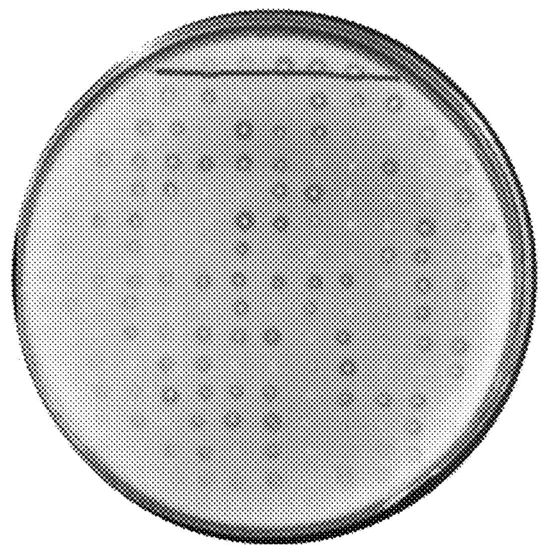
FIG. 5B is a construction view of the flat transparent circle screening method showing the actual mutant library screening.

Example 6 Establishment of High Throughput Screening Method of Monooxygenase AcPSMO Mutant When the compound of Formula IIIa and the co-solvent DMSO are added at a certain ratio, they exhibit a milk-while color in the solution. With substrate consumption and product generation during the reaction progress, the solution will gradually change to transparent. Based on such a phenomenon, a high throughput plate transparent circle screening method is established to determine the oxidative activity of the compound of Formula IIIa. The screening plate is an LB solid plate with 50 μg/mL of kanamycin, a 0.1 mM final concentration of IPTG, 2 mM of the compound of Formula IIIa and 1% v/v of the co-solvent DMSO being added. The screening plate was cultured in a 30° C. constant temperature incubator for 12 h or more, and observed with the production of transparent circle. The potential positive clones with significant transparent circle (bigger than that of the blank control) were selected. The photographs are shown in FIGS. 5A-B.

Example 7 Construction of Thioether Monooxygenase AcPSMO Random Mutants

The error-prone PCR technology was used to construct a random mutation library of thioether monooxygenase AcPSMO: by taking the recombinant plasmid for expressing the monooxygenase AcPSMO mutant shown in SEQ ID NO: 40 prepared in Example 5 as a template and For Nde I and Rev Hind III as a primer, an error-prone PCR was performed with Taq DNA polymerase. In order to obtain a suitable mutation rate, a series of different $MnCl_2$ concentration gradients (100 μM-300 μM $MnCl_2$) were used to construct the mutation library. The PCR reaction conditions are as follows: to a PCR reaction system with a total volume of 50 μL is added 0.5-20 ng of template, 5 μL of 10×PCR buffer (Mg' Plus), 4 μL of dNTP (2.0 mM each), 5 μL of $MnCl_2$ (1 mM), a pair of mutant primers each 2 μL (10 μM), and 0.25 μL of Taq DNA polymerase, and sterile distilled water q.s. to 50 μL. The PCR reaction program: (1) denaturation at 95° C. for 3 min; (2) denaturation at 94° C. for 10 sec; (3) annealing at 60° C. for 30 sec; (4) stretching at 72° C. for 90 sec; repeating steps (2)-(4) for 30 cycles in total, and finally stretching at 72° C. for 10 min. The product was stored at 4° C. After analysis and verification by agarose gel electrophoresis, the PCR product was gelled and purified for recovery. The recovered target genes and pET28a were double digested with restricted endonucleases Nde I and Hind III at 37° C. for 3-5 h. After analysis and verification by agarose gel electrophoresis, the double digested product was gelled and purified for recovery. The resulting linearized pET28a plasmid was ligated to the target gene fragment ligation at 16° C. by T4 DNA ligase. The ligation product was transformed into *E. coli* BL21 (DE3) competent cells which were spread on a plate containing kanamycin, placed in a 37° C. incubator and incubated for about 12-16 h. The transformant on the plate was transferred onto a plate containing 1 mM of kanamycin, 1% (v/v) of DMSO, 0.1 mM of IPTG, 2 mM of substrate (the compound of Formula IIIa), incubated at 37° C. for 12-14 h, and subject to activity screening by the method of Example 6. The transformants that produced transparent circles were expanded in test tubes. The mutants with a higher activity were purified and characterized, and the corresponding genes were sequenced.

The following monooxygenase AcPSMO mutants were obtained:

amino acid sequence shown in SEQ ID NO:58 (the corresponding base sequence is shown in SEQ ID NO:57);

amino acid sequence shown in SEQ ID NO:60 (the corresponding base sequence is shown in SEQ ID NO:59);

amino acid sequence shown in SEQ ID NO:62 (the corresponding base sequence is shown in SEQ ID NO:61);

amino acid sequence shown in SEQ ID NO:64 (the corresponding base sequence is shown in SEQ ID NO:63);

amino acid sequence shown in SEQ ID NO:66 (the corresponding base sequence is shown in SEQ ID NO:65);

amino acid sequence shown in SEQ ID NO:68 (the corresponding base sequence is shown in SEQ ID NO:67);

amino acid sequence shown in SEQ ID NO:70 (the corresponding base sequence is shown in SEQ ID NO:69);

amino acid sequence shown in SEQ ID NO:72 (the corresponding base sequence is shown in SEQ ID NO:71);

amino acid sequence shown in SEQ ID NO:74 (the corresponding base sequence is shown in SEQ ID NO:73);

amino acid sequence shown in SEQ ID NO:76 (the corresponding base sequence is shown in SEQ ID NO:75);

amino acid sequence shown in SEQ ID NO:78 (the corresponding base sequence is shown in SEQ ID NO:77);

amino acid sequence shown in SEQ ID NO:80 (the corresponding base sequence is shown in SEQ ID NO:79);

amino acid sequence shown in SEQ ID NO:82 (the corresponding base sequence is shown in SEQ ID NO:81);

amino acid sequence shown in SEQ ID NO:90 (the corresponding base sequence is shown in SEQ ID NO:89);

amino acid sequence shown in SEQ ID NO:92 (the corresponding base sequence is shown in SEQ ID NO:91);

amino acid sequence shown in SEQ ID NO:94 (the corresponding base sequence is shown in SEQ ID NO:93);

amino acid sequence shown in SEQ ID NO:96 (the corresponding base sequence is shown in SEQ ID NO:95); and amino acid sequence shown in SEQ ID NO:98 (the corresponding base sequence is shown in SEQ ID NO:97).

It should be noted that, the monooxygenase AcPSMO mutant obtained by random mutation in this Example can also be obtained by the directed mutation technology in Example 5 if the amino acid sequence and/or nucleic acid sequence have/has been known by sequencing.

Example 8 Analysis Method

1) Measurement of Oxidative Activity of Monooxygenase AcPSMO and its Mutant on Compound of Formula IIIa Measurement method: to a 500 μL reaction system were added 390 μL of KPB buffer solution (50 mM, pH 9.0), 50 μL of 10 mM substrate solution (the compound of Formula IIIa, with a final concentration of 1 mM, solubilized by DMSO), 10 μL of 10 mM NADPH (with a final concentration of 0.2 mM), and an amount of enzyme solution. The mixture was reacted at 30° C. at 1000 rpm for 10 min. The product (the compound of Formula IIIb) was detected by HPLC for the yield, and the enzyme activity was calculated. Exemplary liquid chromatography conditions are as follows: C18 reverse phase column; mobile phase: acetonitrile:water=53:47; flowrate: 1 mL/min; column temperature: 30° C.; detection wavelength: 254 nm; and detection time: 10 min. The peak time of Formula IIIa and Formula IIIb is 7.5 min and 5.9 min, respectively.

Definition of enzyme activity (U): the amount of enzyme required to catalyze 1 μM product (the compound of Formula IIIb) per minute.

2) Measurement of Oxidative Activity of Monooxygenase AcPSMO and its Mutant on Compound of Formula IIIb Measurement method: to a 500 μL reaction system were added 390 μL of KPB buffer solution (50 mM, pH 9.0), 50 μL of 10 mM solution of the (S)-configuration of the compound of Formula IIIb (with a final concentration of 1 mM, solubilized by DMSO), 10 μL of 10 mM NADPH (with a final concentration of 0.2 mM), and an amount of enzyme solution. The mixture was reacted at 30° C. at 1000 rpm for 10 min. The yield of the compound of Formula IIIc was detected by HPLC, and the enzyme activity was calculated. A chiral column IA column was used, with n-heptane/ethanol (70:30) as a mobile phase and at a flowrate of 1.0 mL/min, a detection temperature of 40° C., a detection wavelength of 300 nm, and a detection time of 20 min. The peak time of the (S)-configurations of the compound of Formula IIIb and the compound of Formula IIIc is 11.2 min and 8.0 min, respectively.

Definition of enzyme activity (U): an amount of enzyme required to catalytically produce 1 μmol of the compound of Formula IIIc per minute.

3) Measurement of Selectivity of Monooxygenase AcPSMO and its Mutant for Asymmetrically oxidizing the compound of Formula IIIa In the present invention, the optical purity is generally expressed by the term "enantiomeric excess" or the symbol "ee", which refers to the excess of one enantiomer relative to the other in the mixture. Unless otherwise specified, when the specification refers to purity or ee value, ">99%" means that the residual substrate or an isomer content cannot be accurately determined because it is below the lower limit of detection. The analysis of the ee value can be achieved by subjecting the extracted product to chiral liquid chromatography analysis. The exemplary liquid chromatography conditions are as follows: a chiral column IA column with n-heptane/ethanol (70:30) as the mobile phase is adopted, the flow rate is 1.0 mL/min, the detection temperature is 40° C., the detection wavelength is 300 nm, and the detection time is 20 min. The peak time of the (9-configuration of the compound of Formula IIIb and the (R)-configuration of the compound of Formula IIIb is 11.2 min and 16.8 min, respectively.

4) Measurement of Formate Dehydrogenase Activity

Measurement method: to a 500 μL cuvette were added 430 μL of KPB buffer solution (50 mM, pH 9.0), 50 μL of 1M sodium formate (aq., with a final concentration of 100 mM), 10 μL of 10 mM $NADP^+$ (aq., with a final concentration of 0.2 mM), and 10 μL of enzyme solution with a suitable concentration. The mixture was detected at 30° C. and 340 nm, and the variation of absorption peak within 1 min (ΔA) was recorded. The enzyme activity was calculated in accordance with the following equation:

$$\text{Enzyme activity } (U)=\Delta A\times V\times\text{dilution ratio}\times 10^3/(\varepsilon\times l),$$

Wherein, V is the volume of the enzyme solution in mL; ε (molar extinction coefficient)=6220 $L\cdot mol^{-1}\cdot cm^{-1}$; and l is optical path in cm.

Definition of enzyme activity (U): an amount of enzyme required to generate 1 μmol of NADPH per minute.

5) Measurement of Isopropanol Dehydrogenase Activity

Measurement method: to a 500 μL cuvette were added 430 μL of KPB buffer solution (50 mM, pH 9.0), 50 μL of 1M isopropanol (aq., with a final concentration of 100 mM), 10 μL of 10 mM $NADP^+$ (aq., with a final concentration of 0.2 mM), and 10 μL of enzyme solution with a suitable concentration. The mixture was detected at 30° C. and 340 nm, and the variation of absorption peak within 1 min (ΔA) was recorded. The enzyme activity was calculated in accordance with the following equation:

$$\text{Enzyme activity } (U)=\Delta A\times V\times\text{dilution ratio}\times 10^3/(\varepsilon\times l),$$

wherein, V is the volume of the enzyme solution in mL; ε (molar extinction coefficient)=6220 $L\cdot mol^{-1}\cdot cm^{-1}$; and l is optical path in cm.

Definition of enzyme activity (U): an amount of enzyme required to generate 1 μmol of NADPH per minute.

Example 9 Monooxygenase AcPSMO Catalyzes the Oxidation of Benzyl Thioether to Produce Benzyl Sulfoxide To 1 mL of potassium phosphate buffer solution (100 mM, pH 9.0) were added 0.1 g of AcPSMO lyophilized enzyme powder (Example 3), 2 mM of compound IIa, DSMO to a final concentration of 2% (v/v), $NADP^+$ 0.1 mM, 0.2 U of Glucose dehydrogenase, and 1.5 e.q. glucose. The reaction was stirred at 28° C. and 180 rpm, and sampled 100 μL intermittently. After sampling, 0.6 mL of ethyl acetate was added for extraction. The extract was dried with anhydrous sodium sulfate, evaporated to remove the solvent, then dissolved in 0.5 mL of isopropanol, and detected by HPLC. The conversion at 24 h is greater than 99%.

Example 10 Monooxygenase AcPSMO Mutant V1 Catalyzes the Oxidation of the Compound of Formula IIIa to Produce Esomeprazole To 100 mL of KPB buffer solution (100 mM, pH 8.5) were added 0.1 g of lyophilized enzyme powder of the monooxygenase AcPSMO mutant V1 (SEQ ID NO:40), 15 U of glucose dehydrogenase, 0.1 g of substrate (the compound of Formula IIIa), 1.5 e.q. dextrose, $NADP^+$ 0.2 mM, and DMSO to a final concentration of 5% (v/v). The reaction was stirred at 28° C. and 180 rpm, and sampled 100 μL intermittently. After sampling, 0.6 mL of ethyl acetate was added for extraction. The extract was dried with anhydrous sodium sulfate, evaporated to remove the solvent, and then dissolved in 0.5 mL of isopropanol. The mixture was analyzed for its conversion of substrate and the ee value of the product. The conversion at 16 h is greater than 99%; the ee value of the product (the (S)-configuration of the compound of Formula IIIb) is greater than 99%, and the level of the by-product sulfone (the compound of Formula IIIc) is 0.4%.

Example 11 Monooxygenase AcPSMO Mutant V2 Catalyzes the Oxidation of the Compound of Formula IIIa to Produce Esomeprazole To 10 mL of KPB buffer solution (100 mM, pH 9.0) were added 0.01 g of lyophilized enzyme powder of monooxygenase AcPSMO mutant V2 (SEQ ID NO:70), 2.5 U of formate dehydrogenase, 0.02 g of substrate (the compound of Formula IIIa), 1.5 e.q. sodium formate, $NADP^+$ 0.2 mM, and t-butyl alcohol to a final concentration of 10% (v/v). The reaction was stirred at 28° C. and 180 rpm, and sampled 100 μL intermittently. After sampling, 0.6 mL of ethyl acetate was added for extraction. The extract was dried with anhydrous sodium sulfate, evaporated to remove the solvent, and then dissolved in 0.5 mL of isopropanol. The mixture was analyzed for its conversion of substrate and the ee value of the product. The conversion at 12 h is greater than 97%; the ee value of the product (the (S)-configuration of the compound of Formula IIIb) is greater than 99%, and the level of the by-product sulfone (the compound of Formula IIIc) is 0.3%.

Example 12 Monooxygenase AcPSMO Mutant V2 Catalyzes the Oxidation of the Compound of Formula IIIa to Produce Esomeprazole To 10 mL of KPB buffer solution (100 mM, pH 9.0) were added 0.03 g of lyophilized enzyme powder of monooxygenase AcPSMO mutant V2 (SEQ ID NO:70), 2.5 U of dextrose dehydrogenase, 0.05 g of substrate (the compound of Formula IIIa), 1.5 e.q. dextrose, $NADP^+$ 0.2 mM, and isooctane to a final concentration of 30% (v/v). The reaction was stirred at 28° C. and 180 rpm, adjusted to pH 9.0 with 1M NaOH solution, and sampled 100 μL intermittently. After sampling, 0.6 mL of ethyl acetate was added for extraction. The extract was dried with anhydrous sodium sulfate, evaporated to remove the solvent, and then dissolved in 0.5 mL of isopropanol. The mixture was analyzed for its conversion of substrate and the ee value of the product. The conversion at 16 h is greater than 97%; the ee value of the product (the (S)-configuration of the compound of Formula IIIb) is greater than 99%, and the level of the by-product sulfone (the compound of Formula IIIc) is 0.4%.

Example 13 Monooxygenase AcPSMO Mutant V3 Catalyzes the Oxidation of the Compound of Formula IIIa to Produce Esomeprazole To 10 mL of KPB buffer solution (100 mM, pH 9.0) were added 0.01 g of lyophilized enzyme powder of monooxygenase AcPSMO mutant V3 (SEQ ID NO:74), 2.5 U of formate dehydrogenase, 0.1 g of substrate (the compound of Formula IIIa), 1.5 e.q. sodium formate, $NADP^+$ 0.2 mM, and methanol to a final concentration of 5% (v/v). The reaction was stirred at 28° C. and 180 rpm, adjusted to pH 9.0 with 1M of NaOH solution, and sampled 100 μL intermittently. After sampling, 0.6 mL of ethyl acetate was added for extraction. The extract was dried with anhydrous sodium sulfate, evaporated to remove the solvent, and then dissolved in 0.5 mL of isopropanol. The mixture was analyzed for its conversion of substrate and the ee value of the product. The conversion at 16 h is greater than 97%; the ee value of the product (the (S)-configuration of the compound of Formula IIIb) is greater than 99%, and the level of the by-product sulfone (the compound of Formula IIIc) is 0.5%.

Example 14 Monooxygenase AcPSMO Mutant V4 Catalyzes the Oxidation of the Compound of Formula IIIa to Produce Esomeprazole To 0.5 L of KPB buffer solution (50 mM, pH 9.0) were added 5 g of lyophilized enzyme powder of monooxygenase AcPSMO mutant V4 (SEQ ID NO:82), 2.5 g of formate dehydrogenase, the substrate (the compound of Formula IIIa) that was continuously added at a flow rate of 7.5 g/L for 16 h to a final concentration of 120 g/L, 1.5 e.q. sodium formate, $NADP^+$ 0.3 mM, methanol to a final concentration of 10% (v/v), and the additive Tween 2%. At 25° C., oxygen gas was periodically supplied for 36 hours, and sampled 100 μL intermittently. After sampling, 0.6 mL of ethyl acetate was added for extraction. The extract was dried with anhydrous sodium sulfate, evaporated to remove the solvent, and then dissolved in 0.5 mL of isopropanol. The mixture was analyzed for its conversion of substrate and the ee value of the product. The conversion at 36 h is greater than 99%; the ee value of the product (the (S)-configuration of the compound of Formula IIIb) is greater than 99%, and the level of the by-product sulfone (the compound of Formula IIIc) is 0.6%.

Example 15 Monooxygenase AcPSMO Mutant V5 Catalyzes the Oxidation of the Compound of Formula IIIa to Produce Esomeprazole To 9 L of KPB buffer solution (50 mM, pH 9.0) were added 100 g of lyophilized enzyme powder of monooxygenase AcPSMO mutant V5 (SEQ ID NO:98), 50 g of formate dehydrogenase, the substrate (the compound of Formula IIIa) that was continuously added at a flow rate of 7.5 g/L for 16 h to a final concentration of 120 g/L, 1.5 e.q. sodium formate, $NADP^+$ 0.2 mM, methanol to a final concentration of 10% (v/v), and the additive Tween 2%. At 25° C., oxygen gas was periodically supplied for 20 hours, and sampled 100 μL intermittently. After sampling, 0.6 mL of ethyl acetate was added for extraction. The extract was dried with anhydrous sodium sulfate, evaporated to remove the solvent, and then dissolved in 0.5 mL of isopropanol. The mixture was analyzed for its conversion of substrate and the ee value of the product. The conversion at 20 h is greater than 97%; the ee value of the product (the (S)-configuration of the compound of Formula IIIb) is greater than 99%, and the level of the by-product sulfone (the compound of Formula IIIc) is 0.9%.

The present invention resolves the crystalline structure of *Acinetobacter* thioether monooxygenase, establishes a high-throughput flat transparent circle screening method, and remarkably increases the catalytic activity of the enzyme and the space-time yield of the catalytic reaction by combining rational design with high-throughput screening.

The monooxygenase of the present invention has a high catalytic activity, and a small addition amount of catalyst in reaction. The reaction scale is not limited to a laboratory scale, and can be industrialized, thereby providing new biocatalyst resources for the industrial synthesis of chiral sulfoxide drugs.

What is claimed is:

1. A monooxygenase, comprising a mutant polypeptide of a parental polypeptide having the amino acid sequence shown in SEQ ID NO:2, wherein the mutant polypeptide has an oxidation activity, mutations of the mutant polypeptide comprise replacements of amino acid residues at specified positions of Xaa143, Xaa326, Xaa426, Xaa432, Xaa433, Xaa435, Xaa438, and Xaa505 and optionally at least one position selected from the group consisting of Xaa21; Xaa40; Xaa55; Xaa70; Xaa145; Xaa156; Xaa185; Xaa220; Xaa244; Xaa246; Xaa248; Xaa249; Xaa277; Xaa281; Xaa386; Xaa388; Xaa390; Xaa405; Xaa430; Xaa465; Xaa468; Xaa488; Xaa489; Xaa490; Xaa497; and Xaa501 of the amino acid sequence shown in SEQ ID NO: 2;

wherein at Xaa143, L is replaced with A or P;
at Xaa326, K is replaced with C or F;
at Xaa426, L is replaced with F or P;
at Xaa432, F is replaced with L or I;
at Xaa433, T is replaced with C or A;
at Xaa435, L is replaced with S;
at Xaa438, S is replaced with I; and
at Xaa505, F is replaced with L.

2. The monooxygenase according to claim 1, wherein the mutations further comprise any one of the following:

a) replacement of amino acid residue(s) at any 1, 2, 3, 4, or 5 positions other than the specified positions;

b) deletion of amino acid residue(s) at any 1, 2, 3, 4, or 5 positions other than the specified positions; and c) insertion of amino acid residue(s) at any 1, 2, 3, 4, or 5 positions other than the specified positions.

3. The monooxygenase according to claim 1, wherein the replacements of the amino acid residues at the specified positions further comprise any one or more of the following replacements:

at the Xaa21, S is replaced with G;
at the Xaa40, T is replaced with A;
at the Xaa55, L is replaced with Y, W, F or N;
at the Xaa70, E is replaced with G;
at the Xaa145, A is replaced with S;
at the Xaa156, E is replaced with G;
at the Xaa185, G is replaced with A or S;
at the Xaa220, M is replaced with R;
at the Xaa244, L is replaced with V or I;
at the Xaa246, F is replaced with Y;
at the Xaa248, L is replaced with E, N, A or W;
at the Xaa249, N is replaced with S;
at the Xaa277, F is replaced with L, V, Y, I or D;
at the Xaa281, F is replaced with V or A;
at the Xaa386, N is replaced with S;
at the Xaa388, I is replaced with F, C, K, G;
at the Xaa390, M is replaced with S, V, I;
at the Xaa405, K is replaced with M;
at the Xaa430, G is replaced with T or S;
at the Xaa465, K is replaced with R;
at the Xaa468, V is replaced with A;

at the Xaa488, E is replaced with K;
at the Xaa489, S is replaced with C;
at the Xaa490, W is replaced with R;
at the Xaa497, P is replaced with S; and
at the Xaa501, N is replaced with Y.

4. The monooxygenase according to claim 3, wherein the replacements of the amino acid residues comprise any of the following replacements:

1) 8 replacements, wherein at the Xaa143, the L is replaced with the P; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
2) 8 replacements, wherein at the Xaa143, the L is replaced with the A; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
3) 9 replacements, wherein at the Xaa143, the L is replaced with the P; at the Xaa244, the L is replaced with the V; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
4) 9 replacements, wherein at the Xaa143, the L is replaced with the P; at the Xaa244, the L is replaced with the I; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
5) 9 replacements, wherein at the Xaa143, the L is replaced with the P; at the Xaa248, the L is replaced with the E; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
6) 9 replacements, wherein at the Xaa143, the L is replaced with the P; at the Xaa248, the L is replaced with the N; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
7) 9 replacements, wherein at the Xaa143, the L is replaced with the P; at the Xaa248, the L is replaced with the A; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
8) 9 replacements, wherein at the Xaa143, the L is replaced with the P; at the Xaa248, the L is replaced with the W; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
9) 9 replacements, wherein at the Xaa143, the L is replaced with the P; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
10) 9 replacements, wherein at the Xaa143, the L is replaced with the P; at the Xaa277, the F is replaced with the V; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
11) 9 replacements, wherein at the Xaa143, the L is replaced with the P; at the Xaa277, the F is replaced with the Y; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
12) 9 replacements, wherein at the Xaa143, the L is replaced with the P; at the Xaa277, the F is replaced with the I; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
13) 9 replacements, wherein at the Xaa143, the L is replaced with the P; at the Xaa277, the F is replaced with the D; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
14) 9 replacements, wherein at the Xaa143, the L is replaced with the P; at the Xaa281, the F is replaced with the V; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
15) 9 replacements, wherein at the Xaa143, the L is replaced with the P; at the Xaa281, the F is replaced with the A; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;
16) 10 replacements, wherein at the Xaa143, the L is replaced with the P; at the Xaa277, the F is replaced with the L; at the Xaa281, the F is replaced with the V; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;

17) 10 replacements, wherein at the Xaa143, the L is replaced with the P; at the Xaa277, the F is replaced with the V; at the Xaa281, the F is replaced with the A; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;

18) 11 replacements, wherein at the Xaa143, the L is replaced with the P; at the Xaa200, the M is replaced with the R; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa465, the K is replaced with the R; at the Xaa505, the F is replaced with the L;

19) 10 replacements, wherein at the Xaa143, the L is replaced with the P; at the Xaa185, the G is replaced with the A; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;

20) 10 replacements, wherein at the Xaa143, the L is replaced with the P; at the Xaa246, the F is replaced with the Y; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;

21) 11 replacements, wherein at the Xaa143, the L is replaced with the P; at the Xaa277, the F is replaced with the L; at the Xaa326, the K is replaced with the C; at the Xaa405, the K is replaced with the M; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa501, the N is replaced with the Y; at the Xaa505, the F is replaced with the L;

22) 10 replacements, wherein at the Xaa143, the L is replaced with the P; at the Xaa156, the E is replaced with the G; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;

23) 10 replacements, wherein at the Xaa143, the L is replaced with the P; at the Xaa249, the N is replaced with the S; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;

24) 10 replacements, wherein at the Xaa143, the L is replaced with the P; at the Xaa40, the T is replaced with the A; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa505, the F is replaced with the L;

25) 11 replacements, wherein at the Xaa143, the L is replaced with the P; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa505, the F is replaced with the L;

26) 12 replacements, wherein at the Xaa143, the L is replaced with the P; at the Xaa246, the F is replaced with the Y; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa505, the F is replaced with the L;

27) 13 replacements, wherein at the Xaa143, the L is replaced with the P; at the Xaa246, the F is replaced with the Y; at the Xaa277, the F is replaced with the L; at the Xaa326, the K is replaced with the C; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa501, the N is replaced with the Y; at the Xaa505, the F is replaced with the L;

28) 14 replacements, wherein at the Xaa143, the L is replaced with the P; at the Xaa246, the F is replaced with the Y; at the Xaa277, the F is replaced with the L; at the Xaa326, the K is replaced with the C; at the Xaa386, the N is replaced with the S; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa501, the N is replaced with the Y; at the Xaa505, the F is replaced with the L;

29) 15 replacements, wherein at the Xaa143, the L is replaced with the P; at the Xaa246, the F is replaced with the Y; at the Xaa277, the F is replaced with the L; at the Xaa326, the K is replaced with the C; at the Xaa386, the N is replaced with the S; at the Xaa388, the I is replaced with the F; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa501, the N is replaced with the Y; at the Xaa505, the F is replaced with the L;

30) 16 replacements, wherein at the Xaa143, the L is replaced with the P; at the Xaa246, the F is replaced with the Y; at the Xaa277, the F is replaced with the L; at the Xaa326, the K is replaced with the C; at the Xaa386, the N is replaced with the S; at the Xaa388, the I is replaced with the K; at the Xaa390, the M is replaced with the I; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa501, the N is replaced with the Y; at the Xaa505, the F is replaced with the L;

31) 16 replacements, wherein at the Xaa143, the L is replaced with the P; at the Xaa246, the F is replaced with the Y; at the Xaa277, the F is replaced with the L; at the Xaa326, the K is replaced with the C; at the Xaa386, the N is replaced with the S; at the Xaa388, the I is replaced with the K; at the Xaa390, the M is replaced with the I; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa488, the E is replaced with the K; at the Xaa489, the S is replaced with the C; at the Xaa490, the W is replaced with the R; at the Xaa505, the F is replaced with the L;

32) 19 replacements, wherein at the Xaa21, the S is replaced with the G; at the Xaa55, the L is replaced with the Y; at the Xaa70, the E is replaced with the G; at the Xaa143, the L is replaced with the P; at the Xaa246, the F is replaced with the Y; at the Xaa277, the F is replaced with the L; at the Xaa326, the K is replaced with the C; at the Xaa386, the N is replaced with the S; at the Xaa388, the I is replaced with the K; at the Xaa390, the M is replaced with the I; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa501, the N is replaced with the Y; at the Xaa505, the F is replaced with the L;

(33) 21 replacements, wherein at the Xaa21, the S is replaced with the G; at the Xaa55, the L is replaced with the Y; at the Xaa70, the E is replaced with the G; at the Xaa143, the L is replaced with the P; at the Xaa185, the G is replaced with the S; at the Xaa246, the F is replaced with the Y; at the Xaa277, the F is replaced with the L; at the Xaa326, the K is replaced with the C; at the Xaa386, the N is replaced with the S; at the Xaa388, the I is replaced with the K; at the Xaa390, the M is replaced with the I; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa497, the P is replaced with the S; at the Xaa501, the N is replaced with the Y; at the Xaa505, the F is replaced with the L;

34) 22 replacements, wherein at the Xaa21, the S is replaced with the G; at the Xaa55, the L is replaced with the Y; at the Xaa70, the E is replaced with the G; at the Xaa143, the L is replaced with the P; at the Xaa145, the A is replaced with the S; at the Xaa185, the G is replaced with the S; at the Xaa246, the F is replaced with the Y; at the Xaa277, the F is replaced with the L; at the Xaa326, the K is replaced with the C; at the Xaa386, the N is replaced with the S; at the Xaa388, the I is replaced with the K; at the Xaa390, the M is replaced with the I; at the Xaa426, the L is replaced with the F; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa497, the P is replaced with the S; at the Xaa501, the N is replaced with the Y; at the Xaa505, the F is replaced with the L; and 35) 23 replacements, wherein at the Xaa21, the S is replaced with the G; at the Xaa55, the L is replaced with the Y; at the Xaa70, the E is replaced with the G; at the Xaa143, the L is replaced with the P; at the Xaa145, the A is replaced with the S; at the Xaa185, the G is replaced with the S; at the Xaa246, the F is replaced with the Y; at the Xaa277, the F is replaced with the L; at the Xaa326, the K is replaced with the C; at the Xaa386, the N is replaced with the S; at the Xaa388, the I is replaced with the K; at the Xaa390, the M is replaced with the I; at the Xaa426, the L is replaced with the F; at the Xaa430, the G is replaced with the T; at the Xaa432, the F is replaced with the L; at the Xaa433, the T is replaced with the A; at the Xaa435, the L is replaced with the S; at the Xaa438, the S is replaced with the I; at the Xaa489, the S is replaced with the C; at the Xaa490, the W is replaced with the R; at the Xaa497, the P is replaced with the S; at the Xaa501, the N is replaced with the Y; at the Xaa505, the F is replaced with the L.

5. The monooxygenase according to claim 1, comprising the amino acid sequence:

shown in SEQ ID NO:24, or
shown in SEQ ID NO: 26, or
shown in SEQ ID NO:32, or
shown in SEQ ID NO:40, or
shown in SEQ ID NO:42, or
shown in SEQ ID NO:44, or
shown in SEQ ID NO:54, or
shown in SEQ ID NO:56, or
shown in SEQ ID NO:58, or
shown in SEQ ID NO:60, or
shown in SEQ ID NO:62, or
shown in SEQ ID NO:64, or
shown in SEQ ID NO:66, or
shown in SEQ ID NO:68, or
shown in SEQ ID NO:70, or
shown in SEQ ID NO:72, or
shown in SEQ ID NO:74, or
shown in SEQ ID NO:76, or
shown in SEQ ID NO:78, or
shown in SEQ ID NO:80, or
shown in SEQ ID NO:82, or
shown in SEQ ID NO:90, or
shown in SEQ ID NO:92, or
shown in SEQ ID NO:94, or
shown in SEQ ID NO:96, or
shown in SEQ ID NO:98.

6. A method of preparing the monooxygenase of claim 1, comprising the following steps: culturing a recombinant expression transformant, and isolating the monooxygenase from the recombinant expression transformant;

wherein the recombinant expression transformant comprises a recombinant expression vector, the recombinant expression vector comprises an isolated nucleic acid, and the isolated nucleic acid encodes the monooxygenase according to claim 1.

7. A method for an asymmetric catalytic oxidation of a prochiral thioether compound to a sulfoxide compound, comprising the step of using the monooxygenase according to claim 1 as a catalyst.

8. The method according to claim 7, wherein the prochiral thioether compound is selected from a compound as represented by any one of the formulae:

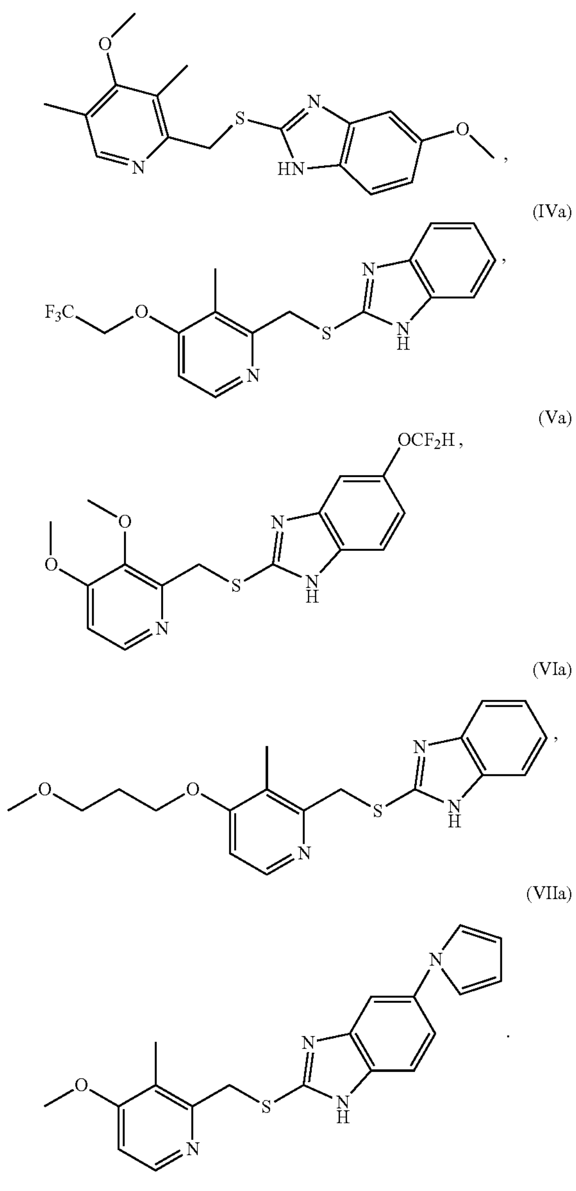

9. The method according to claim 6, wherein the mutations further comprise any one of the following:

a) replacement of amino acid residue(s) at any 1, 2, 3, 4, or 5 positions other than the specified positions;

b) deletion of amino acid residue(s) at any 1, 2, 3, 4, or 5 positions other than the specified positions and c) insertion of amino acid residue(s) at any 1, 2, 3, 4, or 5 positions other than the specified positions.

10. The method according to claim 7, wherein the mutations further comprise any one of the following:

a) replacement of amino acid residue(s) at any 1, 2, 3, 4, or 5 positions other than the specified positions;

b) deletion of amino acid residue(s) at any 1, 2, 3, 4, or 5 positions other than the specified positions; and c) insertion of amino acid residue(s) at any 1, 2, 3, 4, or 5 positions other than the specified positions.

11. The method according to claim 10, wherein the prochiral thioether compound is selected from a compound as represented by any one of the formulae:

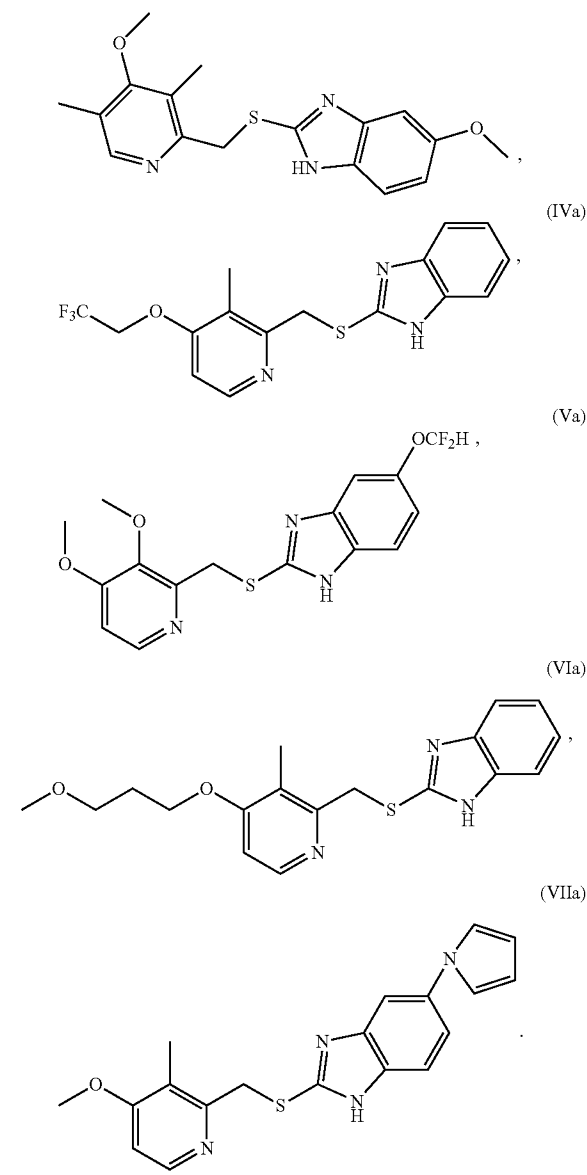

12. The method according to claim 6, wherein the monooxygenase comprises the amino acid sequence:

shown in SEQ ID NO:24, or shown in SEQ ID NO: 26, or shown in SEQ ID NO:32, or shown in SEQ ID NO:40, or
shown in SEQ ID NO:42, or
shown in SEQ ID NO:44, or
shown in SEQ ID NO:54, or
shown in SEQ ID NO:56, or
shown in SEQ ID NO:58, or
shown in SEQ ID NO:60, or
shown in SEQ ID NO:62, or
shown in SEQ ID NO:64, or
shown in SEQ ID NO:66, or
shown in SEQ ID NO:68, or
shown in SEQ ID NO:70, or
shown in SEQ ID NO:72, or
shown in SEQ ID NO:74, or
shown in SEQ ID NO:76, or
shown in SEQ ID NO:78, or
shown in SEQ ID NO:80, or
shown in SEQ ID NO:82, or
shown in SEQ ID NO:90, or
shown in SEQ ID NO:92, or
shown in SEQ ID NO:94, or
shown in SEQ ID NO:96, or
shown in SEQ ID NO:98.

13. The method according to claim 7, wherein the monooxygenase comprises an amino acid sequence:

shown in SEQ ID NO:24, or
shown in SEQ ID NO: 26, or
shown in SEQ ID NO:32, or
shown in SEQ ID NO:40, or
shown in SEQ ID NO:42, or
shown in SEQ ID NO:44, or
shown in SEQ ID NO:54, or
shown in SEQ ID NO:56, or
shown in SEQ ID NO:58, or
shown in SEQ ID NO:60, or
shown in SEQ ID NO:62, or
shown in SEQ ID NO:64, or
shown in SEQ ID NO:66, or
shown in SEQ ID NO:68, or
shown in SEQ ID NO:70, or
shown in SEQ ID NO:72, or
shown in SEQ ID NO:74, or
shown in SEQ ID NO:76, or
shown in SEQ ID NO:78, or
shown in SEQ ID NO:80, or
shown in SEQ ID NO:82, or
shown in SEQ ID NO:90, or
shown in SEQ ID NO:92, or
shown in SEQ ID NO:94, or
shown in SEQ ID NO:96, or
shown in SEQ ID NO:98.

14. The method according to claim 13, wherein the prochiral thioether compound is selected from a compound as represented by any one of the formulae:

Formula IIIa

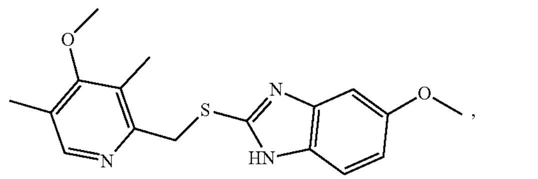

(IVa)

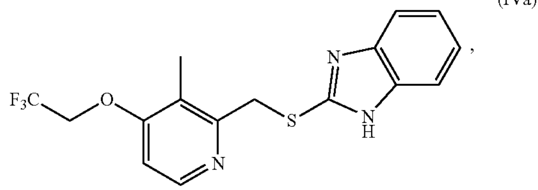

(Va)

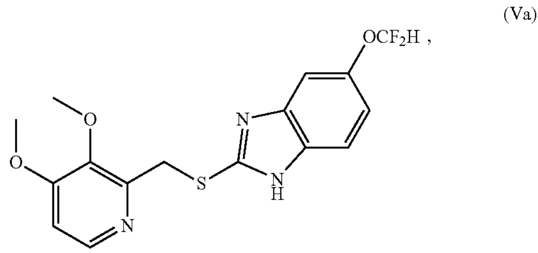

(VIa)

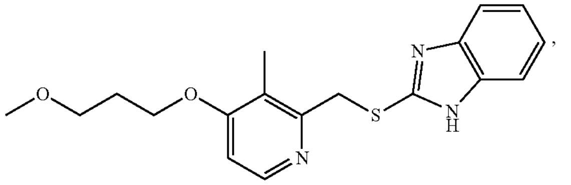

(VIIa)

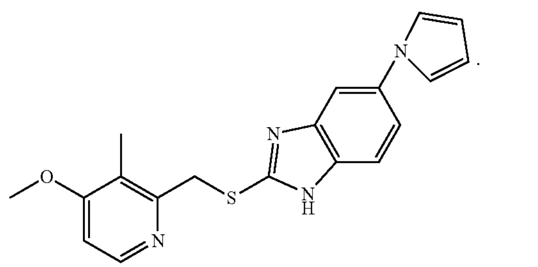

* * * * *